United States Patent [19]

Keenan et al.

[11] Patent Number: 5,177,096

[45] Date of Patent: Jan. 5, 1993

[54] SUBSTITUTED 5-((TETRAZOLYL)ALKENYL)IMIDAZOLES AND PHARMACEUTICAL METHODS OF USE THEREOF

[76] Inventors: Richard M. Keenan, Malvern; Joseph Weinstock, Phoenixville, both of Pa.

[75] Assignee: SmithKline Beecham Corporation, Philadelphia, Pa.

[21] Appl. No.: 590,207

[22] Filed: Sep. 28, 1990

Related U.S. Application Data

[63] Continuation-in-part of Ser. No. 427,158, Oct. 25, 1989, abandoned.

[51] Int. Cl.$^5$ .................... A61K 31/41; C07D 401/12; C07D 403/14; C07D 413/14; C07D 414/14
[52] U.S. Cl. ..................................... 514/381; 514/382; 514/340; 548/252; 548/146; 548/215; 548/240; 546/276
[58] Field of Search ............... 548/252, 146, 215, 240; 514/387, 382, 340; 546/276

[56] References Cited

U.S. PATENT DOCUMENTS

| | | | |
|---|---|---|---|
| 4,340,598 | 7/1982 | Furukawa et al. | 514/400 |
| 4,355,040 | 10/1982 | Furukawa et al. | 514/400 |
| 4,539,410 | 9/1985 | Renfroe | 548/254 |
| 4,880,804 | 11/1989 | Carini et al. | 514/381 |
| 4,882,342 | 11/1989 | von der Saal | 514/381 |

FOREIGN PATENT DOCUMENTS

| | | |
|---|---|---|
| 0103647 | 3/1984 | European Pat. Off. |
| 0236930 | 9/1987 | European Pat. Off. |
| 0253310 | 1/1988 | European Pat. Off. |
| 2651580 | 6/1978 | Fed. Rep. of Germany ...... 514/381 |
| WO86/07054 | 12/1986 | PCT Int'l Appl. |

OTHER PUBLICATIONS

Glennon et al., "N-(phtalimidoalkyl) Derivatives of Serotonergic Agents", J. Med. Chem., vol. 32, pp. 1921–1926 (Aug. 1989).

Glennon et al., "Central Serotonin Receptors as Targets for Drug Research", J. Med. Chem., vol. 30, pp. 1–12 (Jan. 1987).

*Primary Examiner*—David B. Springer
*Attorney, Agent, or Firm*—Mary E. McCarthy; Stephen Venetianer; Edward T. Lentz

[57] ABSTRACT

Angiotensin II receptor antagonists having the formula:

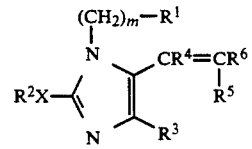

which are useful in regulating hypertension and in the treatment of congestive heart failure, renal failure, and glaucoma, pharmaceutical compositions including these antagonists, and methods of using these compounds to produce angiotensin II receptor antagonism in mammals.

16 Claims, No Drawings

SUBSTITUTED 5-((TETRAZOLYL)ALKENYL)IMIDAZOLES AND PHARMACEUTICAL METHODS OF USE THEREOF

This application is a continuation-in-part of U.S. Ser. No. 07/427,158, filed Oct. 25, 1989, abandoned.

The present invention relates to new substituted 5-[(tetrazolyl)alkenyl]imidazoles which are angiotensin II receptor antagonists and are useful in regulating hypertension induced or exacerbated by angiotensin II, and in the treatment of congestive heart failure, renal failure, and glaucoma. This invention also relates to pharmaceutical compositions containing these compounds and methods for using these compounds as antagonists of angiotensin II, as antihypertensive agents and as agents for treating congestive heart failure, renal failure, and glaucoma.

BACKGROUND OF THE INVENTION

The class of peptide pressor hormone known as angiotensin is responsible for a vasopressor action that is implicated in the etiology of hypertension in man. Inappropriate activity of the renin-angiotensin systems appears to be a key element in essential hypertension, congestive heart failure and in some forms of renal disease. In addition to a direct action on arteries and arterioles, angiotensin II (AII), being one of the most potent endogenous vasoconstrictors known, exerts stimulation on the release of aldosterone from the adrenal cortex. Therefore, the renin-angiotensin system, by virtue of its participation in the control of renal sodium handling, plays an important role in cardiovascular hemostasis.

Interruption of the renin angiotensin system with converting enzyme inhibitors, such as captopril, has proved to be clinically useful in the treatment of hypertension and congestive heart failure (Abrams, W. B., et al., (1984), Federation Proc., 43, 1314). The most direct approach towards inhibition of the renin angiotensin system would block the action of AII at the receptor. Compelling evidence suggests that AII also contributes to renal vasoconstriction and sodium retention that is characteristic of a number of disorders such as heart failure, cirrhosis and complications of pregnancy (Hollenberg, N. K., (1984), J. Cardiovas. Pharmacol., 6, S176). In addition, recent animal studies suggest that inhibition of the renin angiotensin system may be beneficial in halting or slowing the progression of chronic renal failure (Anderson, S., et al., (1985), J. Clin. Invest., 76, 612). Also, a recent patent application (South African Patent Application No. 87/01,653) claims that AII antagonists are useful as agents for reducing and controlling elevated intraocular pressure especially glaucoma, in mammals.

The compounds of this invention inhibit, block and antagonize the action of the hormone AII, and are therefore useful in regulating and moderating angiotensin induced hypertension, congestive heart failure, renal failure and other disorders attributed to the actions of AII. When compounds of this invention are administered to mammals, the elevated blood pressure due to AII is reduced and other manifestations based on AII intercession are minimized and controlled.

Recognition of the importance of blocking and inhibiting the actions of AII has stimulated other efforts to synthesize antagonists of AII. The following references have disclosed imidazole derivatives which are described as having AII blocking activity and useful as hypotensive agents.

Furukawa et al., U.S. Pat. No. 4,340,598 discloses imidazol-5-ylacetic acids and imidazol-5-ylpropanoic acids. Specifically, the discloser includes 1-benzyl-2-n-butyl-5-chloroimidazole-4-acetic acid and 1-benzyl-2-phenyl-5-chloroimidazole-4-propanoic acid.

Furukawa, et al., U.S. Pat. No. 4,355,040 discloses substituted imidazole-5-acetic acid derivatives. A compound specifically disclosed is 1-(2-chlorobenzyl)-2-n-butyl-4-chloroimidazole-5-acetic acid.

Carini et al. in EP 253,310 disclose certain imidazolylalkenoic acids and 5-[(tetrazolyl)alkyl]imidazoles. Two intermediates described in this patent are ethyl 3-[1-(4-nitrobenzyl)-2-butyl-4-chloroimidazol-5-yl]propenoate and ethyl 3-[2-butyl-4-chloro-1-(4-aminobenzyl)imidazol-5-yl]propenoate and a compound specifically disclosed is 2-n-butyl-1-[4-(2-carbomethoxybenzoyl)benzyl]4-chloro-5-[(1H -tetrazol-5-yl)methyl]imidazole.

Also, Wareing, in PCT/EP 86/00297, discloses as intermediates certain imidazolylpropenoate compounds. Specifically, the disclosure includes ethyl 3-[1-(4-fluorophenyl)-4-isopropyl-2-phenyl-1H-imidazol-5-yl]-2-propenoate.

DESCRIPTION OF THE INVENTION

The compounds of the present invention that are blockers of angiotensin II receptors are represented by the following Formula (I):

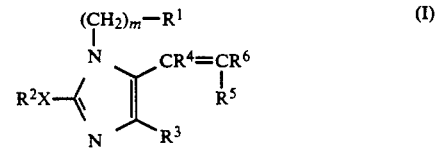

in which:
R[1] is adamantylmethyl, or phenyl, biphenyl, or naphthyl, with each aryl group being unsubstituted or substituted by one to three substituents selected from Cl, Br, F, I, $C_1$-$C_6$alkyl, nitro, $CO_2R^7$, $C_1$-$C_6$alkoxy, hydroxy, $SC_1$-$C_6$alkyl, $SO_2C_1$-$C_6$alkyl, tetrazol-5-yl, $SO_2NHR^7$, $NHSO_2R^7$, $SO_3H$, PO-$(OR^7)_2$, $CONR^7R^7$, CN, $NR^7R^7$, $NR^7COH$, $NR^7COC_1$-$C_6$alkyl, $NR^7CON(R^7)_2$, $NR^7COW$, $SO_2W$, or W;

R[2] is $C_2$-$C_{10}$alkyl, $C_3$-$C_{10}$alkenyl, $(CH_2)_{0-8}$-$C_3$-$C_6$cycloalkyl, or $(CH_2)_{0-8}$phenyl unsubstituted or substituted by one to three substituents selected from $C_1$-$C_6$alkyl, nitro, Cl, Br, F, I, hydroxy, $C_1$-$C_6$alkoxy, $NR^7R^7$, $CO_2R^7$, CN, $CONR^7R^7$, W, $NR^7COH$, $NR^7COC_1$-$C_6$, $NR^7COW$, $SO_2W$, $SO_2C_1$-$C_6$alkyl, or $SC_1$-$C_6$alkyl;

X is a single bond, S, or O;

m is 0–4;

R[3] is hydrogen, Cl, Br, F, I, CHO, hydroxymethyl, $CO_2R^7$, $CONR^7R^7$, $NO_2$, W, $C_1$-$C_6$alkyl, $NR^7R^7$, CN, or phenyl;

R[4] and R[5] are each independently hydrogen, $C_1$-$C_8$alkyl, $C_3$-$C_6$cycloalkyl, thienyl-Y-, furyl-Y-, pyrazolyl-Y-, imidazolyl-Y-, thiazolyl-Y-, pyridyl-Y-, tetrazolyl-Y-, pyrrolyl-Y-, triazolyl-Y-, oxazolyl-Y-, isoxazolyl-Y-, or phenyl-Y-, with aryl or heteroaryl group being unsubstituted or substituted by $C_1$-$C_6$alkyl, $C_1$-$C_6$alkoxy, Cl, Br, F, I, $NR^7R^7$, $CO_2R^7$, OH, $NO_2$, $SO_2NHR^7$, $SO_3H$, $CONR^7R^7$, W, $SO_2W$, $SC_1-C_6$alkyl, $SO_2C_1-C_6$alkyl, $NR^7COH$, $NR^7COW$, or $NR^7COC_1-C_6$alkyl;

Y is $C_1-C_6$alkyl which is straight or branched or a single bond;

$R^6$ is Z-tetrazol-5-yl;

Z is a single bond, vinyl, or methylene unsubstituted or substituted by $C_1-C_4$alkyl, one or two benzyl groups, thienylmethyl, or furylmethyl;

W is $C_nF_{2n+1}$, wherein n is 1-4; and each $R^7$ independently is hydrogen or $C_1-C_6$alkyl; or a pharmaceutically acceptable salt thereof.

Preferably, one of $R^4$ and $R^5$ is hydrogen or $C_1-C_6$ alkyl.

Preferred compounds of this invention are represented by Formula (I) when:

$R^1$ is phenyl unsubstituted or substituted by one to three substituents selected from chloro, fluoro, nitro, methyl, trifluoromethyl, methoxy, hydroxy, sulfonamido, sulfamyl, cyano, carboxy, carbo$C_1-C_6$alkoxy, carbamoyl, or tetrazol-5-yl;

$R^2$ is $C_2-C_8$alkyl;

X is a single bond or S;

m is one or two;

$R^3$ is hydrogen, chloro, fluoro, or trifluoromethyl;

$R^4$ is hydrogen or $C_1-C_4$alkyl;

$R^5$ is thienylmethyl unsubstituted or substituted by methyl, or benzyl unsubstituted or substituted by methoxy or hydroxy; and $R^6$ is tetrazol-5-yl;

or a pharmaceutically acceptable salt thereof.

The E isomers (trans stereochemistry of the tetrazole and imidazole groups) are generally more active and thus, are preferred over the Z isomers (cis).

As used herein, the terms alkyl, alkenyl, alkoxy and alkynyl mean carbon chains which are branched or unbranched with the length of the chain determined by the descriptor preceding the term.

Particular compounds of the invention include, but are not limited to, the following:

(E)-1-[2-n-butyl-1-{(2-chlorophenyl)methyl}-1H-imidazol-5-yl]-2-(1H -tetrazol-5-yl)-3-(2-thienyl)-1-propene, (E)-1-[2-n-butyl-1-{(2-chlorophenyl)methyl}-1H-imidazol-5-yl]-2-(1H-tetrazol-5-yl)-3-(5-methyl-2-thienyl)-1-propene, (E)-1-[2-n-butyl-1-{(2-nitrophenyl)methyl}-1H-imidazol-5-yl]-2-(1H-tetrazol-5-yl)-3-(3-thienyl)-1-propene, (E)-1-[2-n-butyl-1-{(2-trifluoromethylphenyl)methyl}-1H-imidazol-5-yl]-2-(1H-tetrazol-5-yl)-3-(2-thienyl)-1-propene, (E)-1-[2-n-butyl-1-{(2,3-dichlorophenyl)methyl}-1H-imidazol-5-yl]-2-(1H -tetrazol-5-yl)-3-(2-thienyl)-1-propene, (E)-1-[2-n-butyl-1-{(2-chlorophenyl)methyl}-4-fluoro-1H-imidazol-5-yl]-2-(1H -tetrazol-5-yl)-3-(2-thienyl)-1-propene, (E)-1-[2-n-butyl-1-{(2-chlorophenyl)methyl}-1H-imidazol-5-yl]-2-(1H -tetrazol-5-yl)-3-(3-thienyl)-1-propene, (E)-1-[2-n-butyl-1-{(2-chlorophenyl)methyl}-1H-imidazol-5-yl]-2-(1H-tetrazol-5-yl)-3-(4-methoxyphenyl)-1-propene, (E)-1-[2-n-butyl-1-{(2-chlorophenyl)methyl}-1H-imidazol-5-yl]-2-(1H -tetrazol-5-yl)-3-(4-hydroxyphenyl)-1-propene, (E)-2-[2-(1-butenyl)-1-{(2-chlorophenyl)methyl}-1H-imidazol-5-yl[-2-(1H-tetrazol-5-yl)-3(2-thienyl)-1-propene, (E)-1-[2-n-propyl-1-{(2-chlorophenyl)methyl}-1H-imidazol-5-yl]-2-(1H-tetrazol-5-yl)-3-(2-thienyl)-1-propene, (E)-1-[2-n-butyl-1-{(4-(1H-tetrazol-5-yl)phenyl)methyl}-1H-imidazol-5-yl]-2-(1H-tetrazol-5-yl)-3-(2-thienyl)-1-propene, and (E)-1-[2-n-butyl-1-{(4-(carboxyphenyl))methyl}-1H-imidazol-5-yl]-2-(1H-tetrazol-5-yl)-3-(2-thienyl)-1-propene;

or a pharmaceutically acceptable salt thereof.

The invention also relates to pharmaceutical compositions comprising a pharmaceutical carrier and an effective amount of a compound of Formula (I).

Also included in the present invention are methods for antagonizing angiotensin II receptors which comprises administering to a subject in need thereof an effective amount of a compound of Formula (I). Methods of producing antihypertensive activity and methods of treating congestive heart failure, glaucoma, and renal failure by administering these compounds are also included in this invention.

The compounds of this invention are prepared by procedures described herein and illustrated by the examples. Reagents, protecting groups and functionality on the imidazole and other fragments of the molecule must be consistent with the proposed chemical transformations. Steps in the synthesis must be compatible with the functional groups and the protecting groups on the imidazole and other parts of the molecule.

The following procedure is useful for the preparation of compounds of Formula (I) particularly where $R^1$ is 2-chlorophenyl or 4-carboxyphenyl, $R^2$ is n-propyl or n-butyl, X is a single bond or S, m is one or two, $R^3$ is hydrogen, chloro, or fluoro, $R^4$ is hydrogen, $R^5$ is as described in Formula (I), and $R^6$ is tetrazol-5-yl.

The starting materials, 2-$R^2$X-imidazole, are known to the art (J. Org. Chem., 45:4038, 1980) or are synthesized by known procedures. For example, imidazole is converted to 2-n-butylimidazole by reacting imidazole with triethylorthoformate and p-toluenesulfonic acid to give 1-diethoxyorthoamide imidazole and then treating with n-butyl lithium to give the 2-lithium derivative of the orthoamide and alkylating with n-butyl iodide in a suitable solvent, such as tetrahydrofuran (THF).

The 1-$R^1(CH_2)_{1-4}$-group is incorporated onto the 2-$R^2$X-imidazole by known procedures, for example, by reaction with an $R^1$-$(CH_2)_{1-4}$ halide, mesylate or acetate, such as 2-chlorobenzyl bromide, in a suitable solvent, such as dimethylformamide (DMF), in the presence of a suitable acid acceptor, such as sodium alkylate, potassium or sodium carbonate, or a metal hydride, preferably sodium hydride at a reaction temperature of 25° C. to 100° C., preferably 50° C. The resulting 1-$R^1(CH_2)_{1-4}$-2-$R^2$X-imidazole is hydroxymethylated in the 5-position, for example, by reacting with formaldehyde in the presence of sodium acetate in acetic acid to provide the 1-$R^1(CH_2)_{1-4}$-2-$R^2$X-5-hydroxymethylimidazole intermediates.

Alternatively, the 1-$R^1(CH_2)_{1-4}$-2-$R^2$-5-hydroxymethylimidazole intermediates are prepared by reacting an imido ether, $R^2$-C(=NH)-Oalkyl, such as valeramidine methyl ether, with dihydroxyacetone in liquid ammonia under pressure to give 2-$R^2$-5-hydroxymethylimidazole. This intermediate is reacted with acetic anhydride to give 1-acetoxy-5-acetoxymethyl-2-$R^2$X-imidazole. The diacetate intermediate is N-alkylated, for example, using 2-chlorobenzyl triflate and the resulting 1-$R^1(CH_2)_{1-4}$-2-$R^2$-5-acetoxymethylimidazole is treated with aqueous base, such as 10% sodium hydroxide solution, to give the 1-$R^1CH_2$-2-$R^2$-5-hydroxymethylimidazole intermediate.

Compounds wherein the $R^1$ group is directly attached to the nitrogen of the imidazole ring are prepared following the methods described in U.S. Pat. No. 4,194,049. For example, an appropriately substituted benzylamine is reacted with a $R^2$-nitrile, such as valeronitrile, in the presence of a Lewis Acid, such as hydrochloric acid, zinc chloride, or aluminum chloride, in an inert organic solvent, such as tetrahydrofuran, methylene chloride, or toluene, at a temperature of 25° C. to 150° C. The resulting amidine is converted to the 1-$R^1$-2-$R^2$-imidazol-5-carboxaldehyde derivative in a reaction with a halomalonaldehyde, such as bromomalonaldehyde, in an appropriate solvent, such as a $C_1$-$C_4$alcohol. The 5-hydroxymethylimidazole is prepared by reacting the 5-carboxaldehyde compound with a metal hydride reducing agent, such as sodium borohydride, in an organic solvent, such as $C_1$-$C_4$alkyl alcohol.

Alternatively, the 2-$R^1$S-imidazole compounds are prepared by the following procedure. Benzylamines, substituted by one to three substituents selected from halo, $C_{1-6}$alkyl, $C_{1-6}$alkoxy, CN, $NO_2$, $CO_2C_{1-6}$alkyl, $SC_{1-4}$alkyl, $SO_2C_{1-4}$alkyl, or $C_nF_{2n+1}$, wherein n is 1-4, are alkylated with a $C_{1-6}$alkyl chloroacetate, for example methyl chloroacetate, in the presence of a base, such as triethylamine, in a suitable solvent, such as dimethylformamide. The resulting alkylaminoalkyl ester compounds are N-formulated with formic acid in the presence of a suitable solvent, such as xylenes, followed by C-formulation of the carbon alpha to both the amino and the ester groups. Reaction of this intermediate with acidic thiocyanate, preferably potassium thiocyante, in an inert organic solvent, such as a $C_1$-$C_4$alkyl alcohol, produces 1-$RCH_2$-2-mercapto-5-alkanoate ester imidazole compounds. The free thio group of the ester imidazole is reacted with a halo-$R^{10}$ compound, wherein $R^{10}$ is $C_{2-10}$alkyl, $C_{3-10}$alkenyl, $C_{3-10}$alkynyl, $C_3$-$C_6$cycloalkyl or an optionally substituted $(CH_2)_{0-8}$phenyl, preferably propyl bromide, in the presence of a suitable base, such as sodium carbonate, in an appropriate solvent, such as ethyl acetate. The ester is reduced to the hydroxymethylimidazole intermediate by reduction with a suitable reagent, preferable diisobutyl aluminum hydride, in an appropriate solvent, such as tetrahydrofuran, at a temperature of −78° C. to 25° C., preferably at less than −10° C.

The hydroxymethyl group of the hereinbefore prepared intermediates is oxidized to an aldehyde by treatment with a suitable reagent, such as anhydrous chromic acid-silica gel in tetrahydrofuran or, preferably, with activated manganese dioxide, in a suitable solvent such as benzene, xylenes or, preferably, toluene, at a temperature of 25° C. to 140° C., preferably, 100° C. The 1-$R^1(CH_2)_m$)-2-$R^2X$-imidazol-5-carboxaldehydes are reacted with an appropriate phosphonate, such as those listed in Table I (Examples 1-4). The phosphonates are prepared, for example, from trialkyl phosphonoacetates by alkylation with an appropriate halide, mesylate or acetate in the presence of a suitable base, such as sodium hydride, in a suitable solvent, preferably glyme at a reaction temperature of 25° C. to 110° C., preferably at 55° C., to provide, for example, the phosphonates listed in Table 1. The reaction of the imidazol-5-carboxyaldehydes with the phosphonates is performed in the presence of a suitable base, such as a metal alkoxide, lithium hydride or, preferably, sodium hydride, in a suitable solvent, such as ethanol, methanol, ether, dioxane, tetrahydrofuran or, preferably glyme, at a reaction temperature of 10° C. to 50° C., preferably, at 25° C., to provide a variable mixture of trans and cis, e.g., (E) and (Z), 1-$R^1(CH_2)_m$-2-$R^2X$-5-CH=C($R^5$)(COO-alkyl)-imidazoles. These isomers are readily separated by chromatography over silica gel in suitable solvent systems, preferably hexanes in ethyl acetate mixtures. The esters are hydrolyzed to the acids, 1-$R^1$-$(CH_2)_m$-2-$R^2X$-5-CH=C($R^5$)COOH-imidazoles, using bases, such as potassium hydroxide, lithium hydroxide or sodium hydroxide, in a suitable solvent system, such as, for example, aqueous alcohols or diglyme. The trans and cis structures of the acids are readily determined by NMR by the NOE protocol, as well as by the biological activities since, generally, the trans (E) isomeric acids are the more potent isomers.

Formula (I) tetrazole compounds are prepared by the following procedure. The acid compounds, prepared above, are reacted with a halogenating agent, such as thionyl chloride, in a suitable solvent, for example benzene, to give the corresponding acid halide compounds. The acid halides are then converted to primary amide compounds in a reaction with concentrated ammonia. Subsequent dehydration of the amides with oxalyl chloride/dimethylformamide in acetonitrile/dimethylformamide yields the nitrile compounds, which are the immediate precursors to the Formula (I) tetrazole compounds. Tetrazole formation is accomplished by reacting the nitriles with azide, preferably aluminum azide prepared in situ by the reaction of sodium azide with aluminum chloride, in a suitable solvent, for example tetrahydrofuran.

Compounds of Formula (1), wherein $R^6$ is tetrazol-5-yl and $R^1$, $R^2$, $R^3$, $R^4$ and $R^5$ are as described in Formula (I), are also prepared by the following procedure.

The 2-$R^2X$-imidazole starting materials are reacted with trimethylsilylethoxymethyl(SEM) chloride to give 1-(trimethylsilyl)ethoxymethyl-2-$R^2X$-imidazole. The reaction is carried out, for example, in the presence of sodium hydride in a solvent such as dimethylformamide. The 5-tributyltin derivatives are prepared by lithiation with, for example, butyllithium in a suitable solvent, preferably diethyl ether, followed by treatment of the lithio imidazole derivative with a tributyltin halide, preferably tri-N-butyltin chloride, at −10° C. to 35° C., preferably at 25° C. The 1-SEM-2-$R^2X$-5-tributyltinimidazole is coupled with an α,β-unsaturated acid ester having a leaving group on the β-position, such as a halide or trifluoromethanesulfonyloxy group, for example, BrC$R^4$=C($R^5$)(COOalkyl), in the presence of a phosphine ligand, such as bis(diphenylphosphino)propane, or triphenylphosphine and a palladium (II) compound, or preferably tetrakis(triphenylphosphine)palladium(0), and with or without a base, such as tributylamine, at a temperature of 50° C. to 150° C., preferably at 120° C. Both the (E) and (Z) olefinic isomers are prepared by this procedure, and the isomeric esters are readily separated by chromatography over silica gel. The 1-SEM group from the (E) and (Z) isomers is hydrolyzed with acid, for example, aqueous hydrochloric, in a suitable alcoholic solvent, such as methanol or ethanol, and the 1-unsubstituted imidazole derivatives are converted to the 1-t-butoxycarbonyl (t-BOC) imidazoles with di-t-butyl dicarbonate (Hoppe-Seyler's Z. Physiol. Chem., (1976), 357, 1651). The t-BOC esters are alkylated and hydrolyzed with, for example 2-chlorobenzyl-O-triflate, in the presence of a suitable base, preferably diisopropylethylamine, in a suitable solvent, preferably methylene dichloride, to afford the 1-(2-chlorophenyl)methylimidazole derivatives (esters). The (E) and (Z) isomers are hydrolyzed to the (E) and (Z) acids by alkaline hydrolysis and the Formula (I) tetrazole compounds are prepared by the method described above.

Alternatively, the Formula (I) tetrazole compounds are prepared by the following procedure. Starting 2-$R^2X$-imidazol-5-carboxaldehydes are reacted with an N-alkylating protecting reagent, such as chloromethyl pivalate (POM-Cl), in the presence of a base, such as potassium carbonate, in a suitable solvent, such as dimethylformamide, at a temperature of 20° C. to 50° C., preferably at 25° C., to give N-alkylation (e.g., POM derivation) on the latest hindered nitrogen atom of the imidazole nucleus. The 1-$R^1(CH_2)_m$-group is incorporated onto the imidazole by N-alkylation of the above prepared aldehyde with, for example, a halomethylbenzene compound, such as methyl 4-bromomethyl-3-chlorobenzoate, at a temperature of 80° C. to 125° C., preferable at 100° C. The protecting group on the 3-nitrogen of the imidazole ring is removed by base hydrolysis, for example using a biphasic mixture of ethyl acetate and aqueous sodium carbonate, to give 1-$R^1(CH_2)_m$-2-$R^2X$-imidazole-5-carboxaldehyde compounds. The Formula (I) compounds can be prepared from these 5-carboxaldehyde compounds by the methods hereinbefore described.

Compounds of Formula (I) in which $R^1$ is 2-chlorophenyl or 4-carboxyphenyl, $R^2$ is n-propyl or n-butyl, X is a single bond or S, $R^3$ is H, Cl, or $CF_3$, $R^4$ is methyl, $R^5$ is as described in Formula (I), $R^6$ is tetrazol-5-yl and other parameters are as described above are prepared as follows. The 1-$R^1(CH_2)_m$-2-$R^2X$ -imidazol-5-carboxaldehydes, prepared as described above, are converted to the corresponding alcohols with an organometallic derivative or Grignard reagent, preferably methyl lithium, in a suitable solvent, such as tetrahydrofuran. The alcohol is oxidized, for example, using manganese dioxide to give the ketone. The olefinic esters are prepared from the ketone by reaction with appropriate phosphonates to give the (E) and/or (Z) isomers which are readily separated. The acids are prepared from the esters by alkaline hydrolysis and the Formula (I) tetrazole compounds are prepared as described above.

Alternately, compounds of Formula (I) are prepared as follows. The 1-$R^1$-$(CH_2)_m$-2-$R^2X$-imidazol-5-carboxaldehyde is treated with a lithio derivative prepared from the reaction of lithium diisopropyl amide in a suitable solvent, preferably tetrahydrofuran, at −78° C. to −10° C., preferably at −78° C., with an acid ester, such as phenyl-$CH_2$-$CO_2C_{1-6}$alkyl, to give the 5-CH(OH)CH($R^5$)-$CO_2C_{1-6}$alkyl imidazole compound. The hydroxy group of this intermediate is converted to a mesylate or an acetate and the mesylate, or preferably the acetate, is heated in a suitable solvent, such as toluene, with one to two equivalents of 1,8-diazobicyclo[5.4.0]undec-7-ene, at 50° to 110° C., preferably at 80° C., to afford the Formula (I) olefinic ester compound. The (E) isomer is the predominate olefinic isomer. The acids are prepared from the esters by alkaline hydrolysis and the Formula (I) tetrazole compounds are prepared as described above.

Compounds of Formula (I), wherein $R^1$ is 2-chlorophenyl or 4-carboxyphenyl, $R^2$ is n-propyl or n-butyl, X is a single bond or S, $R^3$ is H, Cl, $CF_3$, or $CH_2OH$, $R^4$ is H, $R^5$ is as described in Formula (I) and $R^6$ is tetrazol-5-yl, may be prepared by heating 1-$R^1$-$(CH_2)_m$-2-$R^2X$-imidazol-5-carboxaldehydes at 50° C. to 180° C., preferably at 140° C., with an appropriately substituted phenyl or heterocyclic acetic acid and with acetic anhydride and potassium carbonate to provide unsaturated acids, such as 3-[2-n-butyl-1-(2-chlorophenyl)methyl-1H-imidazol-5-yl]-2-$R^5$-2-propenoic acid. The trans olefinic acid is the principal product. The Formula (I) tetrazole compounds are prepared as described above.

Compounds of Formula (I) in which $R^6$ is -Z-tetrazolyl wherein Z is an optionally substituted methylene group are prepared by reducing the acid group of the trans or (E) isomers of 3-(imidazol-5-yl)-2-propenoic acid esters (prepared as described above) with an appropriate hydride reagent, preferably diisobutylaluminum hydride, in a suitable solvent, such as tetrahydrofuran, to provide the unsaturated alcohol compounds. These compounds are reacted with ethyl chloroformate, for example, with a base, preferably triethylamine, in a suitable solvent, such as tetrahydrofuran, to give 5-EtOOCOCH$_2$C$R^5$=C$R^4$-imidazoles which are reacted with carbon monoxide in the presence of a phosphine ligand, preferably triphenylphosphine with palladium (II) acetate, in a suitable solvent, preferably tetrahydrofuran, at a temperature of 25° C. to 100° C., preferably at 40° C., to give the 5-EtOOCCH$_2$C$R^5$=C$R^4$-imidazoles. The corresponding acids are prepared from these ethyl esters by base hydrolysis as described above, and the Formula (I) tetrazole compounds are prepared by the methods described above.

Compounds of Formula (I) in which Z has an additional substitution on the carbon α to the carboxylate group are prepared by converting 5-EtO$_2$CCH$_2$C$R^5$=C$H^4$-imidazoles to the lithium derivative with a lithium dialkylamide, preferably lithium diisopropylamide, and then treating with an alkylating agent, such as methyl halide, benzyl bromide, or heterocyclic methyl halide, to provide the mono alkylated product compounds or the dialkylated product compounds. The acid compounds are prepared from the esters by base hydrolysis and the Formula (I) tetrazole compounds are prepared by the procedure described above.

Compounds of Formula (I) in which the $R^1$ substituent is substituted by hydroxy are formed from Formula (I) compounds in which the $R^1$ group is substituted by $C_1$-$C_4$alkoxy using an ether cleaving reagent, such as boron tribromide or hydrobromic acid.

Compounds of Formula (I) in which the $R^1$ substituent is substituted by carboxy are prepared as follows. The 1-$R^1$-$(CH_2)_m$-2-$R^2X$-imidazol-5-carboxaldehydes wherein $R^1$ is substituted by $CO_2C_1$-$C_6$alkyl are reacted with the lithium salt of a t-butyl ester, such as $(CH_3)_3$COOC-$CH_2$-Y-(2-thienyl). The intermediate β-hydroxy group of the imidazole t-butyl ester is converted to a mesylate or an acetate and the mesylate, or preferably the acetate, is heated in a suitable solvent, such as toluene, with one to two equivalents of a base, such as 1,8-diazobicyclo[5.4.0]undec-7-ene, at 50° C. to 110° C., preferably at 80° C., to afford vinyl ester t-butyl compounds. The t-butyl ester compound is converted to the corresponding carboxylic acid derivative using acidic hydrolysis, such as trifluoroacetic acid, in a suitable solvent, such as methylene chloride. Tetrazole formation is accomplished from these acids using the methods hereinbefore described. Compounds of Formula (I) in which the $R^1$ substituent is substituted by carboxy are formed from the $CO_2C_1$-$C_6$alkyl intermediates prepared above using basic hydrolysis, such as aqueous sodium or potassium hydroxide in methanol or ethanol.

Pharmaceutically acceptable acid addition salts of compounds of Formula (I) are formed with appropriate organic or inorganic acids by methods known in the art. For example, the base is reacted with a suitable inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

Pharmaceutically acceptable base addition salts of compounds of Formula (I) which have an acidic group are prepared by known methods from organic and inorganic bases, including nontoxic alkali metal and alkaline earth bases, for example, calcium, lithium, sodium, and potassium hydroxide; ammonium hydroxide, and nontoxic organic bases, such as triethylamine, butylamine, piperazine, meglumine, choline, diethanolamine, and tromethamine.

Angiotensin II antagonist activity of the compounds of Formula (I) is assessed by in vitro and in vivo methods. In vitro antagonist activity is determined by the ability of the compounds to compete with $^{125}$I-angiotensin II for binding to vascular angiotensin II receptors and by their ability to antagonize the contractile response to angiotensin II in the isolated rabbit aorta. In vivo activity is evaluated by the efficacy of the compounds to inhibit the pressor response to exogenous angiotensin II in conscious rats and to lower blood pressure in a rat model of renin dependent hypertension.

Binding

The radioligand binding assay is a modification of a method previously described in detail (Gunther et al., Circ. Res. 47:278, 1980). A particular fraction from rat mesenteric arteries is incubated in Tris buffer with 80 pM of $^{125}$I-angiotensin II with or without angiotensin II antagonists for 1 hour at 25° C. The incubation is terminated by rapid filtration and receptor bound $^{125}$I-angiotensin II trapped on the filter is quantitated with a gamma counter. The potency of angiotensin II antagonists is expressed as the $IC_{50}$ which is the concentration of antagonist needed to displace 50% of the total specifically bound angiotensin II.

Aorta

The ability of the compounds to antagonize angiotensin II induced vasoconstriction is examined in the rabbit aorta. Ring segments are cut from the rabbit thoracic aorta and suspended in organ baths containing physiological salt solution. The ring segments are mounted over metal supports and attached to force displacement transducers which are connected to a recorder. Cumulative concentration response curves to angiotensin II are performed in the absence of antagonist or following a 30-minute incubation with antagonist. Antagonist disassociation constants ($K_B$) are calculated by the dose ratio method using the mean effective concentrations. Exemplary of the $K_B$ of compounds of the invention (E isomers) is about 0.5 to about 2 $\mu$M.

Inhibition of pressor response to angiotensin II in conscious rats

Rats are prepared with indwelling femoral arterial and venous catheters and a stomach tube (Gellai et al., Kidney Int. 15:419, 1979). Two to three days following surgery the rats are placed in a restrainer and blood pressure is continuously monitored from the arterial catheter with a pressure transducer and recorded on a polygraph. The change in mean arterial pressure in response to intravenous injections of 250 mg/kg angiotensin II is compared at various time points prior to and following the administration of the compounds intravenously or orally at doses of 3 to 300 mg/kg. The dose of compound needed to produce 50% inhibition of the control response to angiotensin II ($IC_{50}$) is used to estimate the potency of the compounds. The $IC_{50}$ of (E)-3-[2-n-butyl-1-{(2-chlorophenyl)methyl}-1H-imidazol-5-yl]2-(2-thienyl)methyl-2-propenyl tetrazole 8 mg/kg i.v. and 13 mg/kg orally.

Antihypertensive activity

The antihypertensive activity of the compounds is measured by their ability to reduce mean arterial pressure in conscious rats made renin dependent hypertensive by ligation of the left renal artery (Cangiano et al., J. Pharmacol. Exp. Ther. 208:310, 1979). Renal artery ligated rats are prepared with indwelling catheters as described above. Seven to eight days following renal artery ligation, the time at which plasma renin levels are highest, the conscious rats are placed in restrainers and mean arterial pressure is continuously recorded prior to and following the administration of the compounds intravenously or orally.

The intraocular pressure lowering effects employed in this invention may be measure by the procedure described by Watkins, et al., J. Ocular Pharmacol., 1 (2):161-168 (1985).

The compounds of Formula (1) are incorporated into convenient dosage forms, such as injectable preparations, or for orally active compounds, capsules or tablets. Solid or liquid pharmaceutical carriers are employed. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies but, preferably, will be from about 25 mg to about 1 g per dosage unit. When a liquid carrier is used, the preparation will be in the form of a syrup, elixir, emulsion, soft gelatin capsule, sterile injectable liquid, such as an ampoule, or an aqueous or nonaqueous liquid suspension.

For topical ophthalmolgic administration, the pharmaceutical compositions adapted include solutions, suspensions, ointments, and solid inserts. Typical pharmaceutically acceptable carriers are, for example, water, mixtures of water and water-miscible solvents such as lower alkanols or vegetable oils, and water soluble ophthalmologically acceptable non-toxic polymers, for example, cellulose derivatives such as methyl cellulose. The pharmaceutical preparation may also contain non toxic auxiliary substances such as emulsifying, preserving, wetting, and bodying agents, as for example, polyethylene glycols; antibacterial components, such as quarternary ammonium compounds; buffering ingredients, such as alkali metal chloride; antioxidants, such as sodium metabisulfite; and other conventional ingredients, such as sorbitan monolaurate.

Additionally, suitable ophthalmic vehicles may be used as carrier media for the present purpose including conventional phosphate buffer vehicle systems.

The pharmaceutical preparation may also be in the form of a solid insert. For example, one may use a solid water soluble polymer as the carrier for the medicament. Solid water insoluble inserts, such as those prepared from ethylene vinyl acetate copolymer, may also be utilized.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral, parenteral, or topical products.

Doses of the compounds of Formula (I) in a pharmaceutical dosage unit as described above will be an efficacious, nontoxic quantity selected from the range of 0.01-200 mg/kg of active compound, preferably 1-100 mg/kg. The selected dose is administered to a human patient in need of angiotensin II receptor antagonism from 1-6 times daily, orally, rectally, topically, by injection, or continuously by infusion. Oral dosage units for human administration preferably contain from 1 to 500 mg of active compound. Lower dosages are used generally for parenteral administration. Oral administration, is used when safe, effective and convenient for the patient. Topical formulations contain the active compound in an amount selected from 0.0001 to 0.1 (w/v%), preferably from 0.0001 to 0.01. As a topical dosage unit form, an amount of active compound from between 50 ng to 0.05 mg, preferably 50 ng to 5 µg, is applied to the human eye.

The method of this invention of antagonizing angiotensin II receptors in mammals, including humans, comprises administering to a subject in need of such antagonism an effective amount of a compound of Formula (I). The method of this invention of producing antihypertensive activity and the method of treating congestive heart failure, glaucoma, and renal failure comprise administering a compound of Formula (I) to a subject in need thereof an effective amount to produce said activity.

The following examples illustrate preparation of compounds and pharmaceutical compositions of this invention. The examples are not intended to limit the scope of this invention as defined hereinabove and as claimed below.

EXAMPLE 1

(E)-1-[2-n-Butyl-1-{(2-chlorophenyl)methyl}-1H-imidazol-5-yl]-2-(1H-tetrazol-5-yl)-3-(2-thienyl)-1-propene (i) 2-n-butyl-1-(2-chlorophenyl)methyl-1H-imidazole Imidazole was converted to the 1-diethoxyorthoamide derivative by the method of Curtis and Brown, *J. Org. Chem.*, (1980), 45, 20. Imidazole (12.8 g, 0.19 mol) and 118.4 g (0.8 mol) of triethylorthoformate were reacted in the presence of 1 g of p-toluenesulfonic acid to give 20.6 (61%), bp 65°-70° C. (0.1 mm) of 1-diethoxyorthoamide imidazole. This product (24.0 g, 0.14 mol) was dissolved in dry tetrahydrofuran (250 mL), cooled to −40° C. and n-butyl lithium (0.14 mol, 56.4 mL of 2.5M in hexanes) was added at −40° C. to −35° C. After 15 minutes n-butyl iodide (31.1 g, 0.169 mol) was added at −40° C., and the reaction was stirred overnight at ambient temperature. The reaction was partitioned between ether and 0.3N hydrochloric acid, and the organic layer was repeatedly extracted with dilute hydrochloric acid. The combined aqueous extracts were neutralized with sodium bicarbonate solution, extracted with methylene chloride, dried over magnesium sulfate and concentrated. A flash distillation on a Kugelrohr apparatus provided 14.8 g (85%) of 2-n-butylimidazole.

2-n-Butylimidazole (9.7 g, 0.078 mol) was dissolved in methanol (50 mL) and added dropwise to a solution of sodium methoxide (from sodium hydride (2.31 g, 0.0934 mol) in methanol (250 mL)). After one hour the solution was evaporated to dryness, and the sodium salt was taken up in dry dimethylformamide (150 mL) and 2-chlorobenzylbromide (16.3 g, 0.079 mol) was added. The mixture was heated at 50° C. for 17 hours under argon, poured onto ice water and the product was extracted into ethyl acetate. The extract was washed, dried, and concentrated to give 18.5 g of crude product which was chromatographed over silica gel with 2:1 ethyl acetate/hexanes to provide 11.9 g (61%) of 2-n-butyl-1-(2-chlorophenyl)methyl-1H-imidazole as an oil. Thin layer chromatography on silica gel with 4:1 ethyl acetate/hexanes gave an R$_f$ value of 0.59.

(ii)
2-n-butyl-1-(2-chlorophenyl)methyl-5-hydroxymethyl-1H-imidazole

Method 1

A mixture of 2-n-butyl-1-(2-chlorophenyl)methyl-1H-imidazole (95.5 g, 0.384 mol), 37% formaldehyde (500 mL), sodium acetate (80 g) and acetic acid (60 mL) was heated to reflux for 40 hours under argon. The reaction was concentrated in vacuo, and the residue was stirred with 500 mL of 20% sodium hydroxide solution for 4 hours, diluted with water and extracted with methylene chloride. The extract was washed, dried, and concentrated. The crude product (117 g) was flash chromatographed over 600 g of silica gel with a gradient of ethyl acetate to 10% of methanol in ethyl acetate to give 8.3 g of starting material, 24.5 g of a mixture of starting material and product, and 44 g (41%) of 2-n-butyl-1-(2-chlorophenyl)methyl-5-hydroxymethyl-1H-imidazole; mp 86°-88° C. (from ethyl acetate). Further elution provided the bis (4,5-hydroxymethyl) derivative; mp 138°-140° C. (from ethyl acetate).

Method 2

A mixture of valeramidine methyl ether hydrochloride (250 g, 1.66 mol) and dihydroxyacetone (150 g, 0.83 mol) dissolved in liquid ammonia was allowed to stand overnight at room temperature in a pressure vessel, and then heated at 65° C. for 4 hours at 375 psi. The ammonia was allowed to evaporate, and the residue was dissolved in methanol (3 L). The resulting slurry was refluxed with added acetonitrile (1 L). The solution was decanted from the solid ammonium chloride while hot. This procedure was repeated, and the combined acetonitrile extracts were treated with charcoal, filtered hot and the filtrate was concentrated in vacuum to give the dark oil, 2-n-butyl-5-hydroxymethylimidazole (253 g, 1.63 mol, 98%).

This crude alcohol (253 g) was treated with acetic anhydride (400 mL) at −15° C. and then was allowed to warm to ambient temperature with stirring, and then stirred an additional 19 hours. The acetic anhydride was evaporated at reduced pressure, the residue taken up in dichloromethane, and the organic phase was washed with 5% sodium bicarbonate solution and water. The extract was dried over sodium sulfate and concentrated to give 323 g (83%) of 1-acetoxy-4-acetoxymethyl-2-n-butylimidazole.

This diacetate was N-alkylated by the following procedure. To a solution of triflic anhydride (120 mL, 0.71 mol) in dichloromethane (200 mL) at −78° C. under argon was added a solution of diisopropyl ethylamine (128 mL, 0.73 mol) and 2-chlorobenzyl alcohol (104 g, 0.72 mol) in dichloromethane (350 mL) over a period of 20 minutes. After being stirred an additional 20 minutes at −78° C., this solution was then treated with 1-acetoxy-4-acetoxymethyl-2-n-butylimidazole (146 g, 0.61 mol) dissolved in dichloromethane (300 mL) over a 20 minute interval. The mixture was then stirred at ambient temperature for 18 hours and the solvents were evaporated. The residual 2-n-butyl-5-acetoxymethyl-1-(2-chlorophenyl)methyl-1H-imidazole was used without purification for the hydrolysis of the acetate group.

A solution of crude 2-n-butyl-5-acetoxymethyl-1-(2-chlorophenyl)methyl-1H-imidazole (250 g) in methanol (200 mL) was treated with 10% sodium hydroxide solution (700 mL) and the mixture was heated on a steam bath for 4 hours. After cooling, dichloromethane was added, the organic phase was separated, washed with water, dried and concentrated. The residue was dissolved in ether, cooled, and seeded to give the crude product. Recrystallization from ethyl acetate gave 176 g of 2-n-butyl-1-(2-chlorophenyl)methyl-5-hydroxymethyl-1H-imidazole; mp 86°-88° C. This material was identical in all respects to the product prepared by Method 1.

(iii) 2-n-butyl-1-(2-chlorophenyl)methyl-1H-imidazol-5-carboxaldehyde

A solution of 2-n-butyl-1-(2-chlorophenyl)methyl-5-hydroxymethyl-1H-imidazole (5.4 g, 0.0194 mol) in toluene (25 mL) was added to a suspension of activated manganese dioxide (27 g) in toluene (325 mL) which was previously concentrated with a Dean Stark water separator at reflux for one hour. The suspension was heated at 100° C. for 17 hours. The solids were filtered and the filtrate concentrated and flash chromatographed over silica gel with 6:4 hexane/ethyl acetate to afford 4.16 g (78%) of 2-n-butyl-1-(2-chlorophenyl)methyl-1H-imidazol-5-carboxaldehyde, as an oil. NMR and IR were consistent with the structure.

Method A (i) trimethyl 3-(2-thienyl)-2-phosphonopropionate

To a solution of 2 thiophenemethanol (2.28 g, 0.02 mol) in carbon tetrachloride (25 mL) was added triphenylphosphine (6.81 g, 0.026 mol), and the solution was refluxed for 3 hours. The cooled reaction mixture was diluted with hexane (60 mL), chilled and filtered. The concentrated filtrate (4.6 g) was flash chromatographed over silica gel with 7:3 hexane/ethyl acetate to provide 2-chloromethylthiophene (1.52 g, 57%) as an oil.

A suspension of sodium hydride (0.271 g, 11.3 mmol) in dry glyme (40 mL) under argon was treated dropwise with trimethyl phosphonoacetate (1.87 g, 10.3 mmol) in glyme (5 mL). The resulting mixture was stirred at room temperature for 1.5 hours. Then 2-chloromethylthiophene (1.5 g, 11.3 mmol) was added, and the mixture was stirred at 65° C. for 18 hours. The reaction was partitioned between water and ethyl acetate, and the organic layer was washed with water and brine, dried with anhydrous magnesium sulfate and concentrated to 1.9 g of an oil. This was chromatographed over silica gel 4:1 ethyl acetate/hexane to afford 800 mg (28%) of trimethyl 3-(2-thienyl)-2-phosphonopropionate.

(ii) methyl (E)-3-[2-n-butyl-1-[(2-chlorophenyl)methyl]-1H-imidazol-5-yl]-2-(2-thienyl)methyl-2-propenoate To a suspension of sodium hydride (69 mg, 2.87 mmol) in glyme (5 mL) was added dropwise a solution of trimethyl 3-(2-thienyl)-2-phosphonopropionate in glyme (3 mL) under an atomsphere of argon. When the gas evolution had subsided, the mixture was heated to 50° C. for 15 minutes. A solution of 2-n-butyl-1-(2-chlorophenyl)methyl-1H-imidazol-5-carboxaldehyde (0.53 g, 1.92 mmol) in glyme (3 mL) was added, and the mixture was stirred at 60°-65° C. for 5 hours. The cooled reaction was partitioned between water and ethyl acetate, and the organic layer was washed with water, dried, concentrated and flash chromatographed over silica gel to give 336 mg (41%) of methyl (E)-3-[2-n-butyl-1-[(2-chlorophenyl)methyl]-1H-imidazol-5-yl[-2-(2-thienyl)methyl-2-propenoate as an oil whose NMR was entirely consistent with the trans or E form of the olefin.

(iii) (E)-3-[2-n-butyl-1-[(2-chlorophenyl)methyl]-1H-imidazol-5-yl]-2-(2-thienyl)methyl-2-propenoic acid A solution of methyl (E)-3-[2-n-butyl-1-[(2-chlorophenyl)methyl]-1H-imidazol-5-yl]2-(2-thienyl)methyl-2-propenoate propenoate (336 mg, 0.783 mmol) in ethanol (10 mL) was treated with 10% sodium hydroxide solution (4 mL), and the solution was stirred for 3 hours at 25° C. The pH was adjusted to 5 and a solid precipitated. The mixture was diluted with water, cooled and filtered to provide 309 mg of solid. A crystallization from ethyl acetate gave 195 mg (60%) of (E)-3-[2-n-butyl-1-[(2-chlorophenyl)methyl]-1H-imidazol-5-yl]-2-(2-thienyl)methyl-2-propenoic acid; mp 177°-179° C.

(iv) (E)-3-[2-n-butyl-1-[(2-chlorophenyl)methyl]-1H-imidazol-5-yl]-2-(2-thienyl)methyl-2-propenamide To a suspension of (E)-3-[2-n-butyl-1-[(2-chlorophenyl)methyl]-1H-imidazol-5-yl]-2-(2-thienyl)methyl- 2-propenoic acid (1.78 g, 4.3 mmol) in benzene (20 ml) was added thionyl chloride (1.53 g, 12.9 mmol). The resultant mixture was heated to 50° C. for 90 minutes, then evaporated to any oily residue. The reside was taken up in hexane and evaporated again. The solid acid chloride was treated with concentrated ammonium hydroxide (40 ml), broken up with a spatula, and the suspension was stirred for 16 hours at room temperature. The solid was filtered, washed with water, and dried at 50° C. under vacuum to yield 1.62 g (91%) of (E)-3-[2-n-butyl-1-[(2-chlorophenyl)methyl]-1H-imidazol-5-yl]-2-(2-thienyl)methyl-2-propenamide; mp 182°-184° C.

(v)
(E)-3-[2-n-butyl-1-[(2-chlorophenyl)methyl-1H-imidazol-5-yl]-2-(2-thienyl)methyl-2-acrylonitrile To a solution of dimethylformamide (1.1 ml, 14.2 mmol) in acetonitrile (50 ml) was added oxalyl chloride (98%, 1.2 ml, 13.5 mmol) at 0° C. under argon. Bubbling was observed, followed by formation of a white precipitate. After 3 minutes, a solution of (E)-3-[2-n-butyl-1-[(2-chlorophenyl)methyl]-1H-imidazol-5-yl]-2-(2-thienyl)methyl-2-propenamide (2.86 g, 6.91 mmol) in dimethylformamide (20 ml) was added via a cannula, followed by 2×3 ml flask rinses, and the reaction became homogeneous. Five minutes later, pyridine (2.2 ml, 27.2 mmol) was added; the reaction mixture was stirred for an additional 5 minutes at 0° C., then partitioned between ethyl acetate and 50% aqueous ammonium chloride. The ethyl acetate layer was washed with water (2×) and brine. The combined aqueous layers were extracted once with ethyl acetate. The ethyl acetate extracts were combined, dried with anhydrous sodium sulfate and evaporated. Flash chromatogrphay (ethyl acetate/hexane, 1:1) afforded 2.55 g (93%) of (E)-3-[2-n-butyl-1-[(2-chlorophenyl)methyl]-1H-imidazol-5-yl]-2-(2-thienyl)methyl-2-acrylonitrile; mp 97°-98° C.

(vi)
(E)-1-[2-n-butyl-1-{(2-chlorophenyl)methyl}-1H-imidazol-5-yl]2-(1H -tetrazol-5-yl)-3-(2-thienyl)-1-propene Tetrahydrofuran (16 ml) was added slowly under argon with stirring to a mixture of (E)-3-[2-n-butyl-1-[(2-chlorophenyl)methyl-1H-imidazol-5-yl]-2-(2-thienyl)methyl-2-acrylonitrile (2.55 g, 6.44 mmol) and aluminum chloride (1.74 g, 13.0 mmol). Sodium azide (3.83 g, 58.3 mmol) was added all at once, followed by a 2 ml tetrahydrofuran rinse, and the reaction was heated to 65° C. for 22 hours, then cooled to room temperature. The reaction mixture was diluted with ethyl acetate (20 ml) and treated with 10% hydrochloric acid solution (20 ml) with vigorous stirring for 5 minutes. The ethyl acetate layer was washed with water and brine. The combined aqueous layers were extracted once with ethyl acetate. The ethyl acetate layers were combined, dried with anhydrous sodium sulfate and evaporated. The residue was recrystallized (ethyl acetate/ethanol, 10:1) to furnish 0.83 g (27%) of (E)-1-[2-n-butyl-1-[(2-chlorophenyl)methyl-1H-imidazol-5-yl]-2-((1H-tetrazol-5-yl)-3-(2-thienyl)-1-propene hydrochloride. The mother liquors were evaporated and purified via flash chromatography (methylene chloride/methanol, 7:1). The pure tetrazole was suspended in ethyl acetate and treated with 1M etheral hydrochloric acid (16 ml), and filtered with ether rinses to yield another 1.26 g (41%) of (E) 1-[2-n-butyl-1-[(2-chlorophenyl)-methyl-1H-imidazol-5-yl]-2-((1H-tetrazol-5-yl)-3-(2-thienyl)-1-propene hydrochloride (total yield 2.09 g. 68%); mp 189°-191° C.

Method B (i) methyl 3-[2-n-butyl-1-[(2-chlorophenyl)methyl]-1H-imidazol-5-yl]-3-hydroxy-2-[(2-thienyl)methyl]propanoate To a solution of diisopropylamine (1.96 g, 0.0194 mol) in dry tetrahydrofuran (40 mL) held at −78° C. under argon was added n-butyl lithium (7.3 mL, 0.0183 mol of 2.5M in toluene), and the mixture was stirred for 10 minutes. Then, methyl 3-(2-thienyl)propanoate (2.83 g, 0.0166 mol) in tetrahydrofuran (2 mL) was added, and the mixture was stirred for 30 minutes at −78° C. A solution of 2-n-butyl-1-(2-chlorophenyl)methyl-1H-imidazol-5-carboxaldehyde (3 g, 0.0111 mol) in tetrahydrofuran (4 mL) was added, and the resulting mixture was stirred at −78° C. for 30 minutes. The reaction was partitioned between saturated ammonium chloride solution and ether, the organic extract was washed with brine, dried over anhydrous magnesium sulfate and concentrated to 6.67 g of crude product. This was flash chromatographed over 70 g of silica gel with 4:1 ethyl acetate/hexanes to provide 4.03 g (81%) of methyl 3-[2-n-butyl-1-(2-chlorophenyl)methyl-1H-imidazol-5-yl]-3-hydroxy-2-[(2-thienyl)methyl]propanoate.

(ii) methyl 3-acetoxy-3-[2-n-butyl-1-(2-chlorophenyl)methyl-1H-imidazol-5-yl]-2-[(2-thienyl)methyl]propanoate A solution of methyl 3-[2-n-butyl-1-(2-chlorophenyl)-methyl-1H-imidazol-5-yl]-3-hydroxy-2-[(2-thienyl)methyl]propanoate (4.03 g, 9.02 mmol) in dichloromethane (100 mL) was treated with 4-dimethylaminopyridine (0.386 g, 3.16 mmol). Then acetic anhydride (8.5 mL, 9.02 mmol) was added dropwise to the stirred mixture. The mixture was stirred for 18 hours, water (35 mL) was added, the mixture was stirred for 1 hour and then diluted with ether and saturated sodium bicarbonate solution The ether layer was washed with brine, dried with anhydrous magnesium sulfate and evaporated to give the title 3-acetoxy derivative as an oil (4.37 g, 99%).

(iii) methyl (E)-3-[2-n-butyl-1-[(2-chlorophenyl)methyl]-1H-imidazol-5-yl]-2-[(2-thienyl)methyl]propenoate A mixture of methyl 3-acetoxy-3-[2-n-butyl-1-(2-chlorophenyl)methyl-1H-imidazol-5-yl]-2-[(2-thienyl)-methyl]propanoate (4.36 g, 8.92 mmol) in dry toluene (80 mL) was treated with 1,8-diazabicyclo[5,4,0]undec-7-ene (DBU) (3.2 mL, 21.4 mmol), and the resulting solution was heated at 80° C. under argon for 3 hours. The solvent was evaporated, the residue triturated with ether and activated charcoal was added. After filtration, the filtrate was concentrated to 6.29 g of an oil that was chromatographed over silica gel with 65:35 hexane/ethyl acetate to give 2.89 g (76%) of methyl (E)-3-[2-n-butyl-1-[(2-chlorophenyl)methyl]-1H-imidazol-5-yl]-2-(2-thienyl)methyl-2-propenoate whose NMR and TLC (50% ethyl acetate in hexane on silica gel) were identical to the product prepared by Method A.

Basic hydrolysis of this ester (2.88 g, 6.71 mmol) according to Method A (iii) gave 2.59 g (93%) of (E)-3-[2-n-butyl-1-[(2-chlorophenyl)methyl]-1H-imidazol-5- yl]-2-(2-thienyl)methyl-2-propenoic acid; mp 175°–177° C. that was identical to the product from Method A.

The title tetrazole compound is prepared from the above named acid by the procedure described in Method A.

EXAMPLES 2-4

In Table I are listed other examples of 5-[(tetrazolyl)alkenyl]imidazoles prepared from 2-n-butyl-1-(2-chlorophenyl)methyl-1H-imidazol-5-carboxaldehyde by the methods described in Example 1 (Method A). The reagents and products are shown in Table I.

EXAMPLE 5

(E)-1-[2-n-Butyl-1-{(2-chlorophenyl)methyl}-1H-imidazol-5-yl]-2-(1H-tetrazol-5-yl)-3-(3-thienyl)-1-propene The title compound was prepared as described in Example 1, using 3-chloromethylthiophene in place of 2-chloromethylthiophene; mp 142°–144° C.

EXAMPLE 6

(E and Z)-1-[2-n-Butyl-1-{(2-chlorophenyl)methyl}-1H-imidazol-5-yl]-2-(1H-tetrazol-5-yl)-3-(5-methyl-2-furyl)methyl-1-propene

Method A

To a suspension of sodium hydride (0.02 mol) in glyme (30 mL) is added dropwise under argon trimethyl 3-(5-methyl-2-furyl)-2-phosphonopropionate (0.02 mol). After one hour at ambient temperature, 2-n-butyl-1-(2-chlorophenyl)methyl-1H-imidazol-5-carboxaldehyde (0.0137 mol) is added, an the mixture is stirred at 40° C. for one hour. The reaction is quenched with ice water, the product extracted into ether and solvent evaporated to give methyl (E)-3-[2-n-butyl-1-{(2-chlorophenyl)methyl}-1H-imidazol-5-yl]-2-(5-methyl-2-furyl)methyl-2-propenoate. The (E) ester is dissolved in ethanol (4 mL) and 10% sodium hydroxide solution (0.5 mL) is added. The solution is stirred at 25° C. under argon for 17 hours, 10% hydrochloric acid solution is added to pH 3.5 and the solid is filtered, washed with water, and dried at 40° C. in vacuum to give (E)-3-[2-n-butyl-1-{(2-chlorophenyl)methyl}-1H-imidazol-5-yl]-2-(5-methyl-2-furyl)methyl-2-propenoic acid. The title tetrazole compound is prepared as described in Example 1.

TABLE I

Alkenyl Tetrazoles

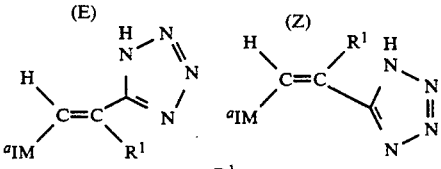

| Example | Reactant[a] | R[1] |
|---|---|---|
| 1 | (MeO)$_2$P(O)CH(CH$_2$-2-thienyl)—COOMe | 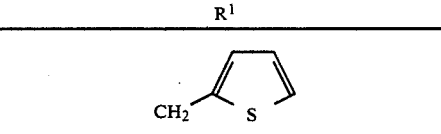 |
| 2 | (MeO)$_2$P(O)CH(CH$_2$-2-furyl)—COOMe[c] | 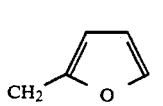 |
| 3 | (MeO)$_2$P(O)CH(CH$_2$-3-furyl)—COOMe[c] | 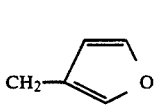 |
| 4 | (MeO)$_2$P(O)CH(CH$_2$-4-(1-tosyl)imidazole)—COOMe[c] | 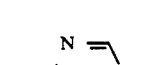 |

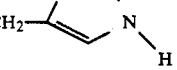

[b]Prepared as in [c];
[c]Reactants for 2–4 prepared as in Method A(i), Example 1 except 2-chloromethylfuran, 3-chloromethylfuran, and 4-acetoxymethyl-1-toxylimidazole are used in place of 2-chloromethylthiophene.

Method B

(i) 2-n-butyl-1-(trimethylsilyl)ethoxymethylimidazole

Hexane washed 80% sodium hydride (1.45 g, 0.0483 mol) in dimethylformamide (80 mL) under argon was treated with a solution of 2-n-butylimidazole (5.45 g, 0.0439 mol) in dimethylformamide (14 mL) dropwise at 25° C. and the reaction was stirred an additional hour. Then 2-(trimethylsilyl)ethoxymethyl chloride (SEM-Cl) (7.68 g, 0.0461 mol) was added, the mixture was stirred for 18 hours at ambient temperature and then partitioned between ice water and ethyl acetate. The washed, dried, concentrated organic solution was chromatographed over silica gel with 1:1 hexane in ethyl acetate to yield 10.8 g (96%) of 2-n-butyl-1-(trimethylsilyl)ethoxymethylimidazole.

(ii) 2-n-butyl-5-tributyltin-1-(trimethylsilyl)ethoxymethylimidazole

A solution of 2-n-butyl-1-SEM imidazole (prepared above) (6.37 g, 0.025 mol) in ethyl ether (125 mL) was treated dropwise with n-butyl lithium (0.0255 mol, 10.2 mL of 2.5M in hexane) under argon at room temperature. After being stirred for an additional 45 minutes, tributyltin chloride (8.83 g, 7.4 mL, 0.026 mol) was added dropwise. The suspension was stirred overnight, saturated ammonium chloride solution was added and the ether layer was separated, washed with brine, dried over sodium sulfate, concentrated and flash chromatographed over silica gel with 3:1 hexane/ethyl acetate to provide 11.3 g (83%) of 2-n-butyl-5-tributyltin-1-(trimethylsilyl)ethoxymethylimidazole.

(iii) ethyl (E and Z)-3-[2-n-butyl-1-{(trimethylsilyl)ethoxymethyl}-1H-imidazol-5-yl]-2-(5-methyl-2-furyl)methyl-2-propenoate To a solution of n-butyl-5-tributyltin-1-(trimethylsilyl)ethoxymethylimidazole (0.0208 mol) in m-xylene (150 mL) is added ethyl 3-bromo-2-(5-methyl-2-furyl)methyl-2-propenoate (0.0233 mol), followed by tetrakis(triphenylphosphine)palladium(0) (0.416 mmol). The reaction mixture is heated at 120° C. for 18 hours under argon. The cooled mixture is washed with water, 10% ammonium hydroxide solution and brine. The solution is treated with charcoal and sodium sulfate, filtered, concentrated and chromatographed over silica gel with 9:1 hexane in ethyl acetate to give ethyl (Z)-3-[2-n-butyl-1-{(trimethylsilyl)ethoxymethyl}-1H-imidazol-5-yl]-2-(5-methyl-2-furyl)methyl-2-propenoate.

(iv) ethyl (E and Z)-3-[3-n-butyl-1-t-butoxycarbonyl-1H-imidazol-5-yl]-2-(5-methyl-2-furyl)methyl-2-propenoate A solution ethyl (E)-3-[2-n-butyl-1-{(trimethylsilyl)ethoxymethyl}-1H-imidazol-5-yl]-2-(5-methyl-2-furyl)methyl-2-propenoate (1.24 g, 3.52 nmol) in ethanol (10 mL) is heated at 60° C. for 3.5 hours with 5N hydrochloric acid solution (20 mL). The cooled reaction is basified with 10% sodium hydroxide solution, extracted with ethyl acetate, washed with water, dried and concentrated. The residue is dissolved in methanol (15 mL), triethylamine (1.5 mL, 10.6 mmol), and di-tert-butyldicarbonate (2.3 g, 10.5 mmol) are added and the mixture is stirred for 18 hours at ambient temperature. The mixture is concentrated in vacuo and chromatographed over silica gel with 4:1 hexane/ethyl acetate to give ethyl (Z)-3-[2-n-butyl-1-t-butoxycarbonyl-1H-imidazol-5-yl]-2-(5-methyl-2-furyl)methyl-2-propenoate as an oil. The (E)-isomer was prepared by the same procedure described as for the (Z)-isomer.

(v) ethyl (E and Z)-3-[2-n-butyl-1-{(2-chlorophenyl)methyl}-1H-imidazol-5-yl]-2-(5-methyl-2-furyl)methyl-2-propenoate To a stirred solution of trifluoromethanesulfonic anhydride (387 mg, 1.37 mmol) in methylene dichloride (1 mL) held at −75° C. under argon is added a solution of 2-chlorobenzyl alcohol (196 mg, 1.37 mmol) and diisopropylethylamine (177 mg, 1.37 mmol) in methylene dichloride (4 mL). After stirring for 20 minutes at −75° C., a solution of ethyl (Z)-3-[2-n-butyl-1-t-butoxycarbonyl-1H-imidazol-5-yl]-2-(5-methyl-2-furyl)methyl-2-propenoate in methylene dichloride (2 mL) is added dropwise over 10 minutes and the mixture was stirred overnight at 25° C. A solution of 5% sodium bicarbonate solution is added with stirring and the layers are separated, washed and dried. The reaction mixture is evaporated to dryness, the residue triturated with 1:1 hexane/ethyl acetate, the solid filtered off and the filtrate is concentrated and chromatographed over silica gel with 7:3 hexane/ethyl acetate to provide the title compound. The title (E)-isomer is prepared by the same procedure described as for the (Z)-isomer.

(vi) (E and Z)-3-[2-n-butyl-1-{(2-chlorophenyl)methyl}-1H-imidazol-5-yl]-2-(5-methyl-2-furyl)methyl-2-propenoic acid The named compounds are prepared by basic hydrolysis of the corresponding ethyl esters according to the procedure described in Example 6, Method A.

(vii) (E and Z)-3-[2-n-butyl-1-{(2-chlorophenyl)methyl}-1H-imidazol-5-yl]-2-(5-methyl-2-furyl)methyl-2-propenyl tetrazole The title tetrazole compounds are prepared as described in Example 1, using the (E and Z)-3-[2-n-butyl-1-{(2-chlorophenyl)methyl}1H-imidazol-5-yl]-2-(5-methyl-2-furyl)methyl-2-propenoic acids as the starting materials.

EXAMPLE 7

(E)-1-[2-n-Butyl-1-{(2-chlorophenyl)methyl}-1H-imidazol-5-yl]-2-(1H-tetrazol-5-yl)-3-(3-thienyl)-1-propene

(i) 2-n-butyl-1-(2-chlorophenyl)methyl-5-(α-hydroxy)ethyl-1H-imidazole

A solution of 2-n-butyl-1-(2-chlorophenyl)methyl-1H-imidazol-carboxaldehyde (Example 1(iii)) (1.1 g, 3.97 mmol) was dissolved in dry tetrahydrofuran (15 mL), cooled to −78° C. under argon and a solution of methyl lithium (3.64 ml of 1.2 M in diethyl ether, 4.57 mmol) was added dropwise. The mixture was stirred for 1.5 hours, quenched with ammonium chloride solution, warmed to ambient temperature and extracted with ethyl acetate. The washed, dried, concentrated product was flashed chromatographed over silica gel with ethyl acetate to provide 1.07 g (92%) of 2-n-butyl-1-(2-chlorophenyl)methyl-5-(α-hydroxy)ethyl-1H-imidazole.

(ii)
[2-n-butyl-1-{(2-chlorophenyl)methyl}-1H-imidazol-5-yl]methyl ketone

A mixture of 2-n-butyl-1-(2-chlorophenyl)methyl-5-(α-hydroxy)ethyl-1H-imidazole (1.07 g, 3.65 mmol), activated manganese dioxide (6 g) and toluene (75 mL) was heated at 90° to 100° C. under a slight vacuum with a Dean Stark water separator for 17 hours. The inorganics were filtered, the concentrated filtrate was applied to a flash silica gel column and the product was eluted with 3:7 hexanes/ethyl acetate to give 0.628 g (59%) of [2-n-butyl-1-{(2-chlorophenyl)methyl}-1H-imidazol-5-yl]methyl-ketone.

(iii) methyl (E)-3-[2-n-butyl-1-{(2-chlorophenyl)methyl}-1H-imidazol-5-yl]-2-(3-thienyl)methyl-2-butenoate To absolute ethanol (3 mL) is added freshly cut sodium (55 mg). Then trimethyl 3-(3-thienyl)-2-phosphonopropionate (2.16 mmol) and [2-n-butyl-1-{(2-chloro phenyl)methyl}-1H-imidazole-5-yl]methyl ketone (0.628 g, 2.16 mmol) are added and the mixture is stirred at 70° C. for 17 hours. The reaction is concentrated, partitioned between ethyl acetate and water, and the organic layer was washed with water, dried, concentrated and chromatographed to afford the title compound.

(iv) (E)-3-[2-n-butyl-1-{(2-chlorophenyl)methyl}-1H-imidazol-5-yl]-2-(3-thienyl)methyl-2-butenoic acid The named compound is prepared according to Example 1 (Method A,iii) by using methyl (E) 3-[2-n-butyl-1-{(2-chlorophenyl)methyl}-1H -imidazol-5-yl]-2-(3-thienyl)methyl-2-butenoate in place of methyl (E)-3-[2-n-butyl-1-{(2-chlorophenyl)methyl}-1H-imidazol-5-yl]-2-(2-thienyl)methyl-2-propenoate.

(v) (E) 1-[2-n-butyl-1-{(2-chlorophenyl)methyl}-1H-imidazol-5-yl]-2-(1H-tetrazol-5-yl)-3-(3-thienyl)-1-propene The title tetrazole compound is prepared as described in Example 1, using (E)-3-[2-n-butyl-1-{(2-chlorophenyl)methyl}-1H-imidazol-5-yl]-2-(3-thienyl)-methyl-2-butenoic acid as the starting material.

EXAMPLE 8

(E)-1-[2-n-Butyl-1-{(2-chloro-6-fluorophenyl)methyl}-1H-imidazol-5-yl]-2-(1H-tetrazol-5-yl)-3-(2-thienyl)-1-propene

(i) 2-n-butyl-1-(2-chloro-6-fluorophenyl)methyl-1H-imidazole

A solution of 2-n-butylimidazole (3.75 g, 0.03 mol) in dry dimethylformamide (4 mL) was added to sodium hydride (0.95 g) in dimethylformamide (18 mL). After the gas evolution subsided, the mixture was stirred one hour under argon and 2-chloro-6-fluorobenzylchloride (5.5. g, 0.031 mol) in dimethylformamide (7 mL) was added to produce an exotherm. The mixture was stirred for 17 hours at ambient temperature, diluted with ice water and extracted with ethyl acetate. The washed, dried, concentrated organic layer provided 7.63 (94%) of the title compound whose NMR was consistent with the structure. This material was used without further purification.

(ii) 2-n-butyl-1-(2-chloro-6-fluorophenyl)methyl-1H-imidazol-5-carboxaldehyde The procedures of Example 1(ii–iii) were used. From 7.63 g of crude 2-n-butyl-1-(2-chloro-6-fluorophenyl)-methyl-1H-imidazole and proportional amounts of other reagents was obtained 2.8 g of 2-n-butyl-1-(2-chloro-6-fluorophenyl)methyl-5-hydroxymethyl-1H-imidazole after chromatography over silica gel with 3% of methanol in methylene chloride; mp 106°–108° C. (from ethyl acetate). This material was oxidized with manganese dioxide and worked up as described above to give 0.88 g (63%) of 2-n-butyl-2-(2-chloro-6-fluorophenyl)methyl-1H-imidazol-5-carboxaldehyde; mp 88°–90° C. (from ethyl acetate).

(iii) (E)-3-[2-n-butyl-1-{(2-chloro-6-fluorophenyl)methyl}-1H-imidazol-5-yl]-2-(2-thienyl)methyl-2-propenoic acid The procedure of Example 1, Method A, is used. 2-n-Butyl-1-(2-chloro-6-fluorophenyl)methyl-1H-imidazole-5-carboxaldehyde, trimethyl 3-(2-thienyl)-2-phosphonopropionate, sodium hydride and glyme are held at 60° C. for 1 hour to give, after chromatography over silica gel with 50% of hexanes in ethyl acetate, methyl (E)-[2-n-butyl-1-{(2-chloro-6-fluorophenyl)methyl}-1H-imidazol-5-yl]-2-(2-thienyl)methyl-2-propenoate and corresponding cis or (Z)-isomer. The (E)-isomer is hydrolyzed to afford (E)-3-[2-n-butyl-1-{(2-chloro-6-fluorophenyl)methyl}-1H-imidazol-5-yl]-2-(2-thienyl)-methyl-2-propenoic acid.

(iv) (E)-1-[2-n-butyl-1-{(2-chloro-6-fluorophenyl)methyl}-1H-imidazol-5-yl]-2-(1H-tetrazol-5-yl)-3-(2-thienyl)-1-propene The title tetrazole compound is prepared as in Example 1, using (E)-3-[2-n-butyl-1-{(2-chloro-6-fluorophenyl)methyl-1H-imidazol-5-yl]-2-(2-thienyl)methyl-2-propenoic acid as the starting material.

EXAMPLE 9

(E)-1-[2-n-Butyl-1-{(2-chlorophenyl)methyl}-1H-imidazol-5-yl]-2-(1H-tetrazol-5-yl)-2-(2-thienyl)-1-ethene A mixture of 2-n-butyl-1-(2-chlorophenyl)methyl-1H-imidazol-5-carboxaldehyde (2 mmol), 2-thienylacetic acid (2.3 mmol), potassium carbonate (0.91 mmol), and acetic anhydride (1 mL) is heated gradually to 140° C. and held at this temperature for 6 hours. The cooled reaction is diluted with water and the solid is separated, triturated several times with ether, and the solid is crystallized to give (E)-3-[2-n-butyl-1-{(2-chlorophenyl)methyl}-1H-imidazol-5-yl]-2-(2-thienyl)-2-propenoic acid. The title tetrazole compound is prepared from this acid by the procedure described in Example 1.

EXAMPLE 10

(E)-1-[2-n-Butyl-1-{(2-chlorophenyl)methyl}-1H-imidazol-5-yl]-2-(1H-tetrazol-5-yl)-2-(2-furyl)-1-ethene This compound is prepared according to Example 9, using 2-furylacetic acid in place of 2-thienylacetic acid.

EXAMPLE 11

(E)-1-[2-n-Butyl-1-{(2-chlorophenyl)methyl}-1H-imidazol-5-yl]-7-(1H-tetrazol-5-yl)-2-(2-thienyl)methyl-1-hexene

(i) Ethyl 3-trifluoromethanesulfonyloxy-2-heptenoate

Ethyl 3-ketoheptanoate (2.07 g, 12 mmol) was dissolved in dimethylformamide (60 mL) under argon and sodium hydride (357 mg, 14.4 mmol) was added. After 30 minutes at room temperature the solid N-phenyltrifluoromethanesulfonamide (*Tetra. Letters,* (1983), 24, 979) (4.97 g, 13.8 mmol) was added. The reaction was stirred for 2 hours, diluted with ether/water and the usual workup gave after chromatography with 5:95 ether/hexane 3.45 g (94%) of ethyl 3-trifluoromethanesulfonyloxy-2-heptenoate.

(ii) ethyl (E)-3-[2-n-butyl-1-{(trimethylsilyl)ethoxymethyl}-1H-imidazol-5-yl]-2-(2-thienyl)methyl-2-heptenoate A solution of 2-n-butyl-5-tributyltin-1-(trimethylsilyl)ethoxymethyl imidazole (Example 6, Method B(ii)) (3.63 mmol) and ethyl 3-trifluoromethanesulfonyloxy-2-(2-thienyl)methyl-2-heptenoate (3.62 mmol) in tetrahydrofuran (5 mL) is added to a mixture of lithium chloride (11.1 mmol) and tetrakis(triphenylphosphine)palladium(0) (0.076 mmol) in tetrahydrofuran (10 mL). The reaction is heated to reflux under argon for 5 hours, cooled, diluted with ether and the ether layer is washed with water, 10% ammonium hydroxide solution and brine. The extract is dried with sodium sulfate and concentrated. The product is chromatographed over silica gel with a gradient of hexane in ethyl acetate to give the title compound.

(iii) ethyl (E)-3-[2-n-butyl-1-{(2-chlorophenyl)methyl}-1H-imidazol-5-yl]-2-(2-thienyl)methyl-2-heptenoate The procedure of Example 6, Method B(iv,v) is followed using ethyl (E)-3-[2-n-butyl-1-(trimethylsilyl)ethoxymethyl}-1H-imidazol-5-yl]-2-(2-thienyl)methyl-2-heptenoate in in place of ethyl (E)-3-[2-n-butyl-1-{(trimethylsilyl)ethoxymethyl}-1H-imidazol-5-yl]-2-(5-methyl-2-furyl)methyl-2-heptanoate to give the title compound.

(iv) (E)-3-[2-n-butyl-1-{(2-chlorophenyl)methyl}-1H-imidazol-5-yl]-2-(2-thienyl)methyl-2-heptenoic acid The ethyl ester, prepared above, is dissolved in ethanol and 10% sodium hydroxide solution is added. An additional 1 ml of base is added incrementally over several hours and the mixture is stirred overnight at room temperature. The cooled reaction was acidified to pH 5 with dilute hydrochloric acid solution, extracted with methylene dichloride and the resulting residue is triturated with ether/hexane to provide the named compound.

(v) (E)-1-[2-n-butyl-1-{(2-chlorophenyl)methyl}-1H-imidazol-5-yl]-7-(1H-tetrazol-5-yl)-2-(2-thienyl)-methyl-1-hexene The title compound is prepared as described in Example 7, using (E)-3-[2-n-butyl-1-{(2-chlorophenyl)methyl-1H-imidazol-5-yl]-2-(2-thienyl)methyl-2-heptenoic acid as the starting material.

EXAMPLE 12

(E)-1-[2-n-Butyl-1-{(2-chlorophenyl)methyl}-1H-imidazol-5-yl]-2-(1H-tetrazol-5-yl)-2-(2-thienyl)methyl-1-propene

(i) Ethyl 4-(3-thienyl)-3-trifluoromethanesulfonyloxy-2-butenoate

This compound was prepared according to Example 11(i) using ethyl 4-(3-thienyl)-3-ketobutanoate in place of ethyl 3-ketoheptanoate.

(ii) ethyl (E)-3-[2-n-butyl-1-{(trimethylsilyl)ethoxymethyl}-1H-imidazol-5-yl]-4-(3-thienyl)-2-butenoate To a solution of 2-n-butyl-1-SEM-imidazole (Example 6, Method B(i)) (5.32-mmol) in ethyl ether (16 mL) is added n-butyl lithium in hexane (6.5 mmol) at a slow rate. After an additional hour of stirring at 25° C., a solution of zinc chloride in ether (6.5 mL of 1.0M) is added followed by tetrahydrofuran (15 mL). After an additional 75 minutes of stirring, the zinc chloride imidazole adduct solution is transferred under argon to a solution of ethyl 4-(3-thienyl)-3-trifluoromethanesulfonyloxybutenoate (6.41 mmol) and tetrakis(triphenylphosphine)palladium(0) (317 mg) in tetrahydrofuran (30 mL). The reaction mixture is stirred at 25° C. for 20 hours and worked up as in Example 12(ii) to provide ethyl (E)-3-[2-n-butyl-1-{trimethylsilyl)ethoxy methyl}-1H-imidazol-5-yl]-4 (3-thienyl)-2-butenoate.

(iii) ethyl (E)-3-[2-n-butyl-1-{(2-chlorophenyl)methyl}-1H-imidazol-5-yl]-4-(3-thienyl)-2-butenoate The title compound is prepared according to the procedure of Example 6, Method B(iv, v) using ethyl (E)-3-[2-n-butyl-1-{(trimethylsilyl)ethoxymethyl}-1H-imidazol-5-yl]-4-(3-thienyl)-2-butenoate in place of ethyl (E)-3-[2-n-butyl-1-{(trimethylsilyl)ethoxymethyl}-1H-imidazol-5-yl]-2-(5-methyl-2-furyl)methyl-2-propenoate. The title compound is an oil.

(iv) (E)-3-[2-n-butyl-1-{(2-chlorophenyl)methyl}-1H-imidazol-5-yl]-4-(3-thienyl)-2-butenoic acid The above ethyl ester (520 mg) is dissolved in ethanol (5 mL) and 5N hydrochloric acid solution (40 mL), and solution is slowly heated at 100° C. with evaporation of the alcohol. After being heated at 100° C. for 6 hours, the reaction is cooled and the white precipitate is collected, air-dried, and then triturated with ether/methanol to afford (E)-3-[2-n-butyl 1-{(2-chlorophenyl)methyl}-1H-imidazol-5-yl]-4-(3-thienyl)-2-butenoic acid hydrochloride.

(v) (E)-1-[2-n-butyl-1-{(2-chlorophenyl)methyl}-1H-imidazol-5-yl]-2-(1H-tetrazol-5-yl)-2-(2-thienyl)methyl-1-propene The title tetrazole compound is prepared as described in Example 1, using (E)-3-[2-n-butyl-1-{(2-chlorophenyl)methyl-1H-imidazol-5-yl]-4-(3-thienyl)-2-butenoc acid as the starting material.

EXAMPLE 13

(E)-1-[2-n-Butyl-1-{(2-chlorophenyl)methyl}-1H-imidazol-5-yl]-3-(1H-tetrazol-5-yl)-2-(5-methyl-2-furyl)-methyl-1-propene (i)

(E)-3-[2-n-butyl-1-{(2-chlorophenyl)methyl}-1H-imidazol-5-yl]-2-(5-methyl-2-furyl)methyl-2-propenol A solution of methyl (E)-3-[2-n-butyl-1-{(2-chlorophenyl)methyl}-1H-imidazol-5-yl]-2-(5-methyl-2-furyl)methyl-2-propenoate (Example 6, Method A) (1.5 mmol) in dry tetrahydrofuran (10 mL) held at −78° C. under argon is treated dropwise with a solution of diisobutyl aluminum hydride in toluene (3.30 mmol, 2.2 mL of 1.5M). The mixture is allowed to warm to ambient temperature and stirred an additional 17 hours. Excess reducing agent is quenched with methanol and water, dilute acetic acid and methylene dichloride are added, and the organic layer is washed with sodium bicarbonate solution, dried and concentrated to give the title compound.

(ii) ethyl
(E)-3-[2-n-butyl-1-{(2-chlorophenyl)methyl}-1H-imidazol-5-yl]-2-(5-methyl-2-furyl)methyl-2-propenyl carbonate To a solution of (E)-3-[2-n-butyl-1-{(2-chlorophenyl)methyl}-1H-imidazol-5-yl]-2-(5-methyl-2-furyl)methyl-2-propenol (6.86 mmol) in methylene chloride (20 mL) and triethylamine (12.4 mmol) cooled to 0° C. under argon is added dropwise ethyl chloroformate (1.34 g, 1.18 ml, 12 mmol). The reaction is then stirred at ambient temperature overnight. Ethyl acetate is added, the precipitate filtered and the concentrated filtrate is flash chromatographed over silica gel with 3:7 hexane/ethyl acetate to provide the title compound.

(iii) ethyl
(E)-4-[2-n-butyl-1-{(2-chlorophenyl)methyl}-1H-imidazole-5-yl]-3-(5-methyl-2-furyl)methyl-3-butenoate A solution of ethyl (E)-3-[2-n-butyl-1-(2-chlorophenyl)methyl}-1H-imidazol-5-yl]-2-(5-methyl-2-furyl)methyl-2-propenyl carbonate (3.77 mmol) in tetrahydrofuran (12 mL) under an atmosphere of carbon monoxide is treated with triphenylphosphine (0.188 mmol) and palladium diacetate and the mixture is heated at 40° C. for 2½ hours. The concentrated reaction mixture is applied to a flash column of silica gel and eluted with 1:1 hexanes/ethyl acetate to afford the title compound.

(iv)
(E)-4-[2-n-butyl-1-{(2-chlorophenyl)methyl}-1H-imidazol-5-yl]-3-(5-methyl-2-furyl)methyl-3-butenoic acid The compound is prepared according to the procedure of Example 1, Method A(iii) using the above prepared ethyl ester in place of ethyl (E)-3-[2-n-butyl-1-{(2-chlorophenyl)methyl}-1H-imidazol-5-yl]-2-(2-thienyl)methyl-2-propenoate.

(v)
(E)-1-[2-n-butyl-1-{(2-chlorophenyl)methyl}-1H-imidazol-5-yl]-3-methyl and -3,3-dimethyl-3-(1H-tetrazol-5-yl-2-(2-thienyl)methyl-1-propene The title tetrazole compound is prepared as described in Example 1, using (E)-4-[2-n-butyl-1-{(2-chlorophenyl)methyl}-1H-imidazol-5-yl-3-(5-methyl-2-furyl)-methyl-3-butenoic acid as the starting material.

EXAMPLE 14

(E)-1-[2-n-Butyl-1-{(2-chlorophenyl)methyl}-1H-imidazol-5-yl]-3-methyl- and -3,3-dimethyl-3-(1H-tetrazol-5-yl)-2-(2-thienyl)methyl-1-propene (i) ethyl
(E)-4-[2-n-butyl-1-{(2-chlorophenyl)methyl}-1H-imidazol-5-yl]-2-methyl-3-(2-thienyl)methyl-3-butenoate Lithium diisopropylamide (0.85 mmol, 1M in tetrahydrofuran) is cooled to −78° under argon and a solution of ethyl (E)-4-[2-n-butyl-1-[(2-chlorophenyl)methyl}-1H-imidazol-5-yl]-3-(2-thienyl)methyl)-3-butenoate (0.709 mmol), prepared as in Example 13 using methyl (E) 3-[2-n-butyl-1-[(2-chlorophenyl)methyl]-1H-imidazol-5-yl]-(2-thienyl)methyl-2-propenoate (Example 1), in tetrahydrofuran (5 mL) is added. After 10 minutes methyl iodide (0.71 mmol) is added. The mixture is then stirred at room temperature overnight, diluted with 10% ammonium chloride and extracted with ethyl acetate. The dried, concentrated product is chromatographed over silica gel with 6:4 hexanes/ethyl acetate to give the title compound. (ii) (E)-1-[2-n-butyl-1-{(2-chlorophenyl)methyl}-1H-imidazol-5-yl]-3-methyl-3-(1H-tetrazol-5-yl)-2-(2-thienyl)methyl-1-propene A solution of the above prepared ethyl ester in ethanol is heated to reflux with 10% sodium hydroxide solution for 2 -hours. The ethanol is evaporated, water is added and the aqueous layer is extracted with ether. The water layer is acidified to pH 1 with dilute hydrochloric acid solution, extracted with ethyl acetate, dried and concentrated to a solid. Trituration with ether provides the hydrochloride salt of (E)-4-[2-n-butyl-1-{(2-chlorophenyl)methyl)-1H-imidazol-5-yl]-2-methyl-3-(2-thienyl)methyl-3-butenoic acid. The title tetrazole compound is prepared as described in Example 1.

(iii)
(E)-1-[2-n-butyl-1-(2-chlorophenyl)methyl}-1H-imidazol-5-yl]-3,3-dimethyl-3-(1H-tetrazol-5-yl)-2-thienyl)methyl-1-propene (E)-4-[2-n-Butyl-1-{(2-chlorophenyl)methyl}-1H-imidazol-5-yl]-2,2-dimethyl-3-(2-thienyl)methyl-3-butenoic acid is prepared according to the procedure of Example 14(i,ii) using two equivalents of methyl-iodide. The title tetrazole compound is prepared as described in Example 1.

EXAMPLE 15

(E)-1-[2-n-Butyl-1-{(2-chlorophenyl)methyl}-1H-imidazol-5-yl]-3-(1H-tetrazol-5-yl)-2-(2-thienyl)methyl-3-(2-thienyl)methyl-1-propene (E)-4-[2-n-Butyl-1-{(2-chlorophenyl)methyl}-1H-imidazol-5-yl]-2-(2-thienyl)methyl-3-(2-thienyl)methyl-3-butenoic acid is prepared according to the procedure of Example 14(i,ii) using less than one equivalent of 2-chloromethylthiophene in place of methyl-iodide. The title tetrazole compound is prepared as described in Example 1.

EXAMPLE 16

(E)-1-[2-n-Butyl-1-(2-chlorophenyl)methyl}-1H-imidazol-5-yl]-3-benzyl-3-(1H-tetrazol-5-yl)-2-(2-thienyl)methyl-1-propene (E)-4-[2-n-Butyl-1-{(2-chlorophenyl)methyl}-1H-imidazol-5-yl]-2-benzyl-3-(2-thienyl)methyl-3-butenoic acid is prepared according to Example 14(i,ii) using less than one equivalent of benzyl bromide at higher solvent dilution. The title tetrazole compound is prepared as described in Example 1.

EXAMPLE 17

(E,E)-1-[2-n-Butyl-1-{(2-chlorophenyl)methyl}-1H-imidazol-5-yl]-4-(1H-tetrazol-5-yl)-2-(2-thienyl)methyl-1,3-butadiene (i) Ethyl (E,E)-5-[2-n-butyl-1-{(2-chlorophenyl)methyl}-1H-imidazol-5-yl]-4-(2-thienyl)methyl-2,4-pentadienoate This compound is prepared according to the procedure of Example 1, Method A, from 3-mmol of 2-n-butyl-1 (2-chlorophenyl)methyl-1H-imidazol-5-carboxaldehyde, 3.75 mmol of triethyl 4-(2-thienyl)methyl-4-phosphonocrotonate, 4.5 mmol of sodium hydride, and 10 mL of glyme is obtained after flash chromatography ethyl (E,E)-5-[2-n-butyl-1-{(2-chlorophenyl)methyl}-1H-imidazol-5-yl]-4-(2-thienyl)methyl-2,4-pentadienoate.

(ii) (E,E)-5-[2-n-butyl-1-(2-chlorophenyl)methyl}-1H-imidazol-5-yl]-4-(2-thienyl)methyl-2,4-pentadienoic acid This compound is prepared according to the procedure of Example 1, Method A(iii) using the above prepared ethyl ester.

Alternately, the sodium salt of the acid is isolated directly from the reaction mixture, prior to neutralization. The crude basic reaction solution is applied to a reverse-phase flash column equilibrated with water. The inorganics are washed from the column with water (3 void volumes) and then the product is eluted with a 50:50 mixture of acetonitrile in water. The acetonitrile is removed in vacuo and then the desired sodium salt is obtained after lyophilization.

(iii) (E,E)-1-[2-n-butyl-1-{(2-chlorophenyl)methyl}-4-hydroxymethyl-(1H-imidazol-5-yl)-2-(1H-tetrazol-5-yl)-3-(2-thienyl)methyl-1,3-butadiene The title tetrazole compound is prepared as described in Example 1, using (E,E)-5-[2-n-butyl-1-{(2-chlorophenyl)methyl}-1H-imidazol-5-yl]-4-(2-thienyl)methyl-2,4-pentadioic acid as the starting material.

EXAMPLE 18

(E)-1-[2-n-Butyl-1-[(2-chlorophenyl)methyl]-4-hydroxymethyl-1H-imidazol-5-yl]-2-(1H-tetrazol-5-yl)-3-(2-thienyl)-1-propene (i) 2-n-butyl-1-(2-chlorophenyl)methyl-4-(t-butyldimethylsilyloxy)methyl-1H-imidazol-5-carboxaldehyde A solution of 2-n-butyl-1-(2-chlorophenyl)methyl-4,5-bis(hydroxy)methyl-1H-imidazole (Example 1(ii)) (310 mg, 1 mmol) in methylene dichloride (5 mL) was treated with 4-dimethylaminopyridine (5.2 mg), triethylamine (1.5 mmol) and t-butyl dimethylsilyl chloride (192 mg, 1.24 mmol). The mixture was stirred at 25° C. for 20 hours, diluted with water and the organic layer was washed well with water, dried, concentrated and chromatographed over silica gel with an ethyl acetate/methanol gradient to afford 127 mg (24%) of the bis (4,5-t-butyldimethylsilyl) ether and 252 mg (59%) of 2-n-butyl-1-(2-chlorophenyl)methyl-4-t-butyldimethysilyloxymethyl-5-hydroxymethyl-1H-imidazole. This monoether (252 mg) was oxidized to the 5-carboxaldehyde using manganese dioxide as described in Example 1(iii) to provide 170 mg of 2-n-butyl-1-(2-chlorophenyl)methyl-4-(t-butyldimethylsilyloxy)methyl-1H-imidazol-5-carboxaldehyde as an oil.

(ii) ethyl (E)-3-[2-n-butyl-1-{(2-chlorophenyl)methyl}-4-(t-butyldimethylsilyloxy)methyl-1H-imidazol-5-yl]-2-(2-thienyl)methyl-2-propenoate In tetrahydrofuran (80 mL) is added n-butyl lithium (15.5 mmol in hexanes) and at −78° C. under argon is then added diisopropylamine (2.4 mL, 17.1 mmol). Methyl 3-(2-thienyl)propanoate (15.3 mmol) is added neat over 5-6 minutes, and the mixture was stirred an additional 30 minutes at −78° C. A solution of 2-n-butyl-1-(2-chlorophenylmethyl-4-(t-butyldimethylsilyloxy)methyl-1H-imidazol-5-carboxaldehyde (10.2 mmol) in tetrahydrofuran (10 mL) is added via cannula, and the reaction mixture is stirred for 15 minutes. The reaction is partitioned between saturated ammonium chloride and ether, and the ether layer is washed with water, dried and concentrated to give crude product. This is chromatographed over silica gel with 20-50% of ethyl acetate in hexanes to afford a mixture of isomeric β-hydroxyester products. A solution of this mixture (8.54 mmol) in methylene dichloride (100 mL) is treated with 4-dimethylaminopyridine (3 mmol) followed by acetic anhydride (84 mmol), and the solution is stirred at room temperature for 5 hours. The reaction is poured into water, stirred for 20 minutes and the product is extracted into ether. The ether extracts are washed with dilute hydrochloric acid solution, water, sodium bicarbonate solution and brine. The dried, concentrated mixture of acetoxyester products is used directly in the elimination reaction. To a solution of the β-acetoxyester product (4.5 mmol) in toluene (60 mL) is added of 1,8-diazabicyclo[5.4.0]undec-7-ene (DBU) (10.9 mmol), and the mixture is heated at 90° C. for 24 hours. The reaction is concentrated to 10 mL, diluted with ether and flash filtered through a 14×3 cm plug of silica gel with ether rinses to afford the crude olefinic product. Chromatography over silica gel with an ethyl acetate in hexanes gradient gives homogeneous ethyl (E)-3-[2-n-butyl-1-{(2-chlorophenyl)methyl}-4-(t-butyldimethylsilyloxy)methyl-1H-imidazol-5-yl]-2-(2-thienyl)methyl-2-propenoate. The elimination of the acetate with DBU produces predominantly the trans (E)-isomer.

(iii) (E)-3-[2-n-butyl-1-{(2-chlorophenyl)methyl}-4-(t-butyldimethylsilyloxy)methyl-1H-imidazol-5-yl]-2-(2-thienyl)methyl-2-propenoic acid A solution of ethyl (E)-3-[2-n-butyl-1-{(2-chlorophenyl)methyl}-4-(t-butyldimethylsilyloxy)methyl-1H-imidazol-5-yl]-2-(2-thienyl)methyl-2-propenoate (0.287 mmol) in absolute ethanol (3 mL) is treated portionwise with one equivalent of 10% sodium hydroxide solution. After being stirred overnight at 25° C., the reaction is heated to 50° C. for 4 hours, then concentrated in vacuo. The residual product is taken up in water, acidified to pH 5–6 and extracted with methylene dichloride. The isolated, dried, concentrated product is triturated with methanol/ether to provide the title compound.

(iv)

(E)-1-[2-n-butyl-1-{(2-chlorophenyl)methyl}-4-(t-butyldimethylsilyoxy)methyl-1H-imidazol-5-yl]-2-(1H-tetrazol-5-yl)-3-(2-thienyl)-1-propene The title compound is prepared as described in Example 1, using (E)-3-[2-n-butyl-1-{(2-chlorophenyl)methyl}-4-(t-butyldimethylsilyloxy)methyl-1H-imidazol-5-yl]-2-(2-thienyl)methyl-2-propenoic acid as the starting material.

(v)

(E)-1-[2-n-butyl-1-{(2-chlorophenyl)methyl}-4-hydroxymethyl-1H-imidazol-5-yl]-2-(1H-tetrazol-5-yl)-3-(2-thienyl)-1-propene The title compound is prepared by reacting (E)-1-[2-n-butyl-1-{(2-chlorophenyl)methyl}-4-(t-butyldimethylsilyoxy)methyl-1H-imidazol-5-yl]-2-(1H-tetrazol-5-yl)-3-(2-thienyl)-1-propene with dilute hydrochloric acid.

EXAMPLE 19

(E)-1-[2-n-Butyl-1-{(2-chlorophenyl)methyl}-1H-imidazol-5-yl]-3-(4-pyridyl)-2-(1H-tetrazol-5-yl)-1-propene (i)

methyl-3-[2-n-butyl-1-(2-chlorophenyl)methyl-1H-imidazol-5-yl]-3-hydroxy-2-[(4 pyridyl)methyl]propanoate To a solution of diisopropylamine (3.58 mL, 25.6 mmol) in dry tetrahydrofuran (50 mL) held at 78° C. under argon was added n-butyl lithium (10.2 mL, 25.6 mmol of 2.5M in toluene), and the mixture was stirred for 10 minutes. Then, methyl 3-(4-pyridyl)propanoate (4.22 g, 25.6 mmol) (prepared by reaction of 4-pyridine carboxaldehyde with trimethyl phosphonoacetate in the presence of sodium hydride in ethylene glycol dimethyl ether, followed by catalytic hydrogenation of the double bond with 10% palladium on carbon at 3 atmosphere of hydrogen in an ethyl acetate solution (98%) to provide the saturated acid) was added in tetrahydrofuran (40 mL) and this mixture was stirred for 30 minutes at −78° C. A solution of 2-n-butyl-1-(2-chlorophenyl)methyl-1H-imidazol-5-carboxaldehyde (5.9 g, 21.3 mmol) in tetrahydrofuran (10 mL) was added and stirring was continued for 30 minutes at −78° C. The reaction was partitioned between saturated ammonium chloride solution and ether, the organic extract was washed with brine, dried over magnesium sulfate, concentrated and flash chromatographed over silica gel with 5% methanol in ethyl acetate to provide 3.32 g (30%) of methyl 3-[2-n-butyl-1-(2-chlorophenyl)methyl-1H-imidazol-5-yl]-3-hydroxy-2-[(4-pyridyl)methyl]-propanoate. TLC on silica gel with 5% methanol in ethyl acetate showed a homogenous product with an R$_f$ of 0.79.

(ii)

methyl-3-acetoxy-3-[2-n-butyl-1-(2-chlorophenyl)methyl-1H-imidazol-5-yl]-2-[(4-pyridyl)methyl]propanoate A solution of methyl-3-[2-n-butyl-1-(2-chlorophenyl)methyl-1H-imidazol-5-yl]-3-hydroxy-2-[(4-pyridyl)methyl]propanoate (3.32 g, 7.5 mmol) dichloromethane (50 mL), 4-dimethylaminopyridine (150 mg, 1.3 mmol) and acetic anhydride (7.1 mL, 75 mmol) was stirred at ambient temperature for 18 hours. Water (5 mL) was added, the mixture was stirred for 2 hours and then diluted with dichloromethane and 5% sodium bicarbonate solution. The organic phase was washed with 5% sodium bicarbonate solution and brine, dried and concentrated to give 4 g of the crude title compound. TLC on silica gel with 5% methanol methyl-acetate showed essentially one spot material with an R$_f$ of 0.86. No starting material was detected. This material was not purified further.

(iii)

methyl-(E)-3-[2-n-butyl-1-{(2-chlorophenyl)methyl}-1H-imidazol-5-yl]-2-[(4-pyridyl)methyl]-2-propenoate A mixture of methyl-3-acetoxy 3-[2-n-butyl-1-(2-chlorophenyl)methyl-1H-imidazol-5-yl]-2-[(4-pyridyl)-methyl]propenoate (7.5 mmol), toluene (50 mL) and 1,8-diazabicyclo[5.4.0]undec-7-ene (DBU) (3.4 mL, 22.5 mmol) was heated at 90° C. for 18 hours under argon. The cooled mixture was diluted with ether, and washed with brine, dried and concentrated to 3.1 g (97%) of the title compound. NMR showed that the trans or E isomer was the primary product.

(iv)

(E)-3-[2-n-butyl-1-[(2-chlorophenyl)methyl}-1H-imidazol-5-yl]-2-(4-pyridyl)methyl-2-propenoic acid A solution of methyl-(E)-3-[2-n-butyl-1-(2-chlorophenyl)methyl}-1H-imidazol-5-yl]-2-(4-pyridyl)methyl-2-propenoate (3.1 g, 7.3 mmol) in ethanol (16 mL) was treated with 10% sodium hydroxide solution and the mixture was stirred for 18 hours at 25° C. The solution was concentrated in vacuum, water was added, the pH was adjusted to 6.5 and the resulting solid was filtered, washed with water and crystallized from methanol/ether to afford 0.48 g of (E)-3-[2-n-butyl-1-{(2-chlorophenylmethyl}-1H-imidazol-5-yl]-2-(4-pyridyl)-methyl-2-propenoic acid; mp 178°–182° C. (d).

(v)

(E)-1-[2-n-butyl-1-{1-(2-chlorophenyl)methyl}-1H-imidazol-5-yl]-3-(4-pyridyl)-2-(1H-tetrazol-5-yl)-1-propene The title tetrazole compound is prepared as described in Example 1, using (E)-3-[2-n-butyl-1-{(2-chlorophenyl)methyl}-1H-imidazol-5-yl]-2-(4-pyridyl)methyl-2-propenoic acid as the starting material.

EXAMPLES 20–24

In Table II are listed other examples of 5-[(tetrazolyl)alkenyl]imidazoles prepared by the methods described in Example 19 (i–v). The starting materials and products are shown in Table II.

TABLE II

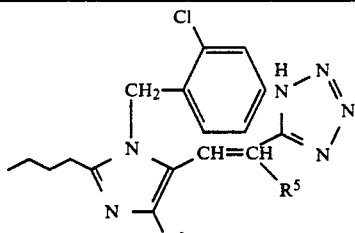

| Example | Starting Materials | R³ | Product (R⁵)ᵃ |
|---|---|---|---|
| 20 | (structure shown; compound II with 2-chlorobenzyl, n-butyl imidazole CHO) ; S-CH₂CH₂CH₂CO₂Me (methyl 4-(2-thienyl)butanoate) | H | —CH₂—(2-thienyl) |
| 21 | (II) ; pyridyl-CH₂CH₂COOMe | H | —CH₂—(pyridyl) |
| 22 | (II) ; pyridyl-CH₂CH₂COOMe | H | —CH₂—(pyridyl) |
| 23 | (II) ; 3-methyl-2-thienyl-CH₂CH₂COOMe | Cl | —CH₂—(3-methyl-2-thienyl) |
| 24 | (structure shown; compound with Cl on imidazole, 2-chlorobenzyl, CHO) ; S-CH₂CH₂COOMe | Cl | —CH₂—(2-thienyl) |

ᵃProduct prepared by the 5 step synthetic route described in Example 19. The olefinic ester is purified, if necessary, by chromatography over silica gel with ethyl acetate/hexane or methanol/ethyl acetate mixtures.

EXAMPLE 25

(E)-1-[2-n-Butyl-1-{(2-chlorophenyl)methyl}-1H-imidazol-5-yl]-3-(5-methyl-2-thienyl)-2-(1H-tetrazol-5-yl)-1-propene The title compound was prepared as described in Example 19, using methyl-3-(5-methyl-2-thienyl)-propanoate in place of methyl-3-(4-pyridyl)propenoate; mp 151°–153° C.

EXAMPLE 26

By the procedure of Example 19 (i–v) using in place of methyl 3-(4-pyridyl)propanoate, the following:
methyl 3-(4-thiazolyl)propanoate,
methyl 3-(1,2,3,4-tetrazol-5-yl)propanoate, and
methyl 3-(1-tosylpyrazol-3-yl)propanoate; the products are:

(E)-1-[2-n-butyl-1-{(2-chlorophenyl)methyl}-1H-imidazol-5-yl]-2-(1H-tetrazol-5-yl)-3-(4-thiazolyl)-1-propene,
(E)-1-[2-n-butyl-1-{(2-chlorophenyl)methyl}-1H-imidazol-5-yl]-3-{1H-tetrazol-5-yl)-2-(1H-tetrazol-5-yl}-1-propene, and
(E)-1-[2-n-butyl-1-{(2-chlorphenyl)methyl}-1H-imdiazol-5-yl]-3-(3-pyrazolyl-2-(1H-tetrazol-5-yl)-1-propene.

EXAMPLE 27

(E)-1-[2-n-Butyl-1-{(2-chlorophenyl)methyl}-4-fluoro-1H-imidazol-5-yl]-2-(1H-tetrazol-5-yl)-3-(2-thienyl)-1-propene By the procedure of Example 19 (i–v) using 2-n-butyl-1-(2-chlorophenyl)methyl-4-fluoro-1H-imidazol-5-carboxaldehyde and methyl 3-(2-thienyl)propanoate as the starting materials, the title compound was prepared. The product was isolated as an amorphous solid.

EXAMPLE 28

(E)-1-[2-n-Butyl-1-{(2-chlorophenyl)methyl}-4-bromo-1H-imidazol-5-yl]-2-(1H-tetrazol-5-yl)-3-(2-thienyl)-1-propene By the procedure of Example 27 using the corresponding 4-bromo starting material, the title compound is prepared.

EXAMPLE 29

(E)-1-[2-n-Butyl-{(2-chlorophenyl)methyl}-4-trifluoromethyl)-1H-imidazol-5-yl]-(1H-tetrazol-5-yl)-3-(2-thienyl)-1-propene Using 2-n-butyl-1-(2-chlorophenyl)methyl-4-trifluoromethyl-1H-imidazol-5-carboxaldehyde (prepared by treating the corresponding 4-bromo compound with trifluoromethyl iodide and copper) in the procedure of Example 19 gives the title compound.

EXAMPLE 30

By the procedure of Example 1, using in place of chlorobenzyl bromide, the following:
2-methylbenzyl bromide,
3-methoxybenzyl bromide,
4-phenylbenzyl bromide,
4-methoxy-3-methylbenzyl bromide,
3-nitrobenzyl bromide, and
2-methoxybenzyl bromide;
and using the phosphonopropionate of Example 1, (MeO)$_2$P(O)CH(CH$_2$-2-thienyl)COOMe, the following products are obtained:
(E)-1-[2-n-butyl-1-{(2-methylphenyl)methyl}-1H-imidazol-5-yl]-2-(1H-tetrazol-5-yl)-3-(2-thienyl)-1-propene,
(E)-1-[2-n-butyl-1-{(3-methoxyphenyl)methyl}-1H-imidazol-5-yl]-2-(1H-tetrazol-5-yl)-3-(2-thienyl)-1-propene,
(E)-1-[2-n-butyl-1-{(4-phenylphenyl)methyl}-1H-imidazol-5-yl]-2-(1H-tetrazol-5-yl)-3-(2-thienyl)-1-propene,
(E)-1-[2-n-butyl-1-{(4-methoxy-3-methylphenyl)methyl}-1H-imidazol-5-yl]-2-(1H-tetrazol-5-yl)-3-(2-thienyl)-1-propene,
(E)-1-[2-n-butyl-1-{(3-nitrophenyl)methyl}-1H-imidazol-5-yl]-2-(1H-tetrazol-5-yl)-3-(2-thienyl)-1-propene, and
(E)-1-[2-n-butyl-1-{(2-methoxyphenyl)methyl}-1H-imidazol-5-yl]-2-(1H-tetrazol-5-yl)-3-(2-thienyl)-1-propene.

EXAMPLE 31

Each of the following methyl esters of propenoates are prepared as in Example 30:
methyl (E)-3-[2-n-butyl-1-{(4-methoxyphenyl)methyl}-1H-imidazol-5-yl]-2-(2-thienyl)methyl-2-propenoate,
methyl (E)-3-[2-n-butyl-1-{(2-methoxyphenyl)methyl}-1H-imidazol-5-yl]-2-(2-thienyl)methyl-2-propenoate, and
methyl-(E)-3-[2-n-butyl-1-{(4-methoxy-3-methylphenyl)methyl}-1H-imidazol-5-yl]-2-(2-thienyl)methyl-2-propenoate.

Each of these esters are treated with boron tribromide in methylene chloride at room temperature for six hours and then each reaction mixture is condensed and treated with a mixture of ethyl acetate and water. The washed ethyl acetate layer gives on evaporation:
(E)-3-[2-n-butyl-1-{(4-hydroxyphenyl)methyl}-1H-imidazol-5-yl]-2-(2-thienyl)methyl-2-propenoic acid,
(E)-3-[2-n-butyl-1-{(2-hydroxyphenyl)methyl}-1H-imidazol-5-yl]-2-(2-thienyl)methyl-2-propenoic acid, and
(E)-3-[2-n-butyl-1-[(4-hydroxy-3-methylphenyl)methyl}-1H-imidazol-5-yl]-2-(2-thienyl)methyl-2-propenoic acid.

The tetrazole compounds of these acids are prepared by the procedure of Example 1 to give:
(E)-1-[2-n-butyl-1-{(4-hydroxyphenyl)methyl}-1H-imidazol-5-yl]-2-(1H-tetrazol-5-yl)-3-(2-thienyl)-1-propene,
(E)-1-[2-n-butyl-1-{(2-hydroxyphenyl)methyl}-1H-imidazol-5-yl]-2-(1H-tetrazol-5-yl)-3-(2-thienyl)-1-propene,
(E)-1-[2-n-butyl-1-{(4-hydroxy-3-methylphenyl)methyl}-1H-imidazol-5-yl]-2-(1H-tetrazol-5-yl)-2-(2-thienyl)-1-propene,

EXAMPLE 32

(E)-1-[2-n-Butyl-1-{(2-nitrophenyl)methyl}-1H-imidazol-5-yl]-2-(1H-tetrazol-5-yl)-3-(2-thienyl)-1-propene The title compound was prepared by the procedure of Example 1 using 2-nitrobenzyl bromide in place of 2-chlorobenzyl bromide; mp 231°–234° C.

EXAMPLE 33

(E)-1-[2-n-Butyl-1-{(2-trifluoromethylphenyl)methyl}-1H-imidazol-5-yl]-2-1H-tetrazol-5-yl)-3-(2-thienyl)-1-propene The title compound was prepared by the procedure of Example 1, using 2-trifluoromethylbenzyl bromide in place of 2-chlorobenzyl bromide. The product was isolated as its hydrochloride salt; mp 206°–208° C.

EXAMPLE 34

(E)-1-[2-n-Butyl-1-{(2,3-dichlorophenyl)methyl}-1H-imidazol-5-yl]-2-(1H-tetrazol-5-yl)-3-(2-thienyl)-1-propene The title compound was prepared by the procedure of Example 1, using 2,3-dichlorobenzyl bromide in place of 2-chlorobenzyl bromide; mp 204°–205° C.

EXAMPLE 35

(E)-1-[2-(1-Butenyl)-1-{(2-chlorophenyl)methyl}-1H-imidazol-5-yl]-2-(1H-tetrazol-5-yl)-3-(2-thienyl)-1-propene A mixture of 2-n-butyl-1-(2-chlorophenyl)methyl-1H-imidazol-5-carboxaldehyde and N-bromosuccinimide in carbon tetrachloride is irradiated to give the 2-(1 bromobutyl)imidazole which is dehydrobrominated by treating 1,8-diazabicyclo[4.5.0]undec-1-ene in tetrahydrofuran to give 2-(1-butenyl)-1-(2-chlorophenyl)methyl-1H-imidazol-5-carboxaldehyde.

Using the above prepared intermediate and the phosphonopropionate of Example 1 in the procedure of gives the title compound.

EXAMPLE 36

(E)-1-[2-Phenyl-1-{(2-chlorophenyl)methyl}-1H-imidazol-5-yl]-2-(1H-tetrazol-5-yl)-3-(2-thienyl)-1-propene By the procedure of Example 1(ii) Method 2, using benzamidine methyl ether in place of valeramidine methyl ether, 2-phenyl-5-hydroxymethylimidazole is prepared and converted to 2-phenyl-1-(2-chlorophenyl)methyl-5-hydroxymethyl-1H-imidazole. The 5-hydroxymethyl-group is oxidized using manganese dioxide by the procedure of Example 1 (iii). The resulting 2-phenyl-1-(2-chlorophenyl)methyl-1H-imidazol-5-carboxaldehyde is used in the procedure of Example 19 with methyl-3-(2-thienyl)propanoate to give the title compound.

EXAMPLE 37

By the procedure of Example 36 using the following amidine methyl ethers:

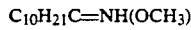

and

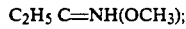

the following products are obtained:
(E)-1-[2-decyl-1-{(2-chlorophenyl)methyl}-1H-imidazol-5-yl]-2-(1H-tetrazol-5-yl) 3-(2-thienyl)-1-propene and
(E)-1-[2-ethyl-1-{(2-chlorophenyl)methyl}-1H-imidazol-5-yl]-2-(1H-tetrazol-5-yl)-3-(2-thienyl)-1-propene

EXAMPLE 38

(E)-1-[2-n-Butyl-1-{(2-chlorophenyl)methyl}-4-formyl-1H-imidazol-5-yl]-2-(1H-tetrazol-5-yl)-3-(2-thienyl)-1-propene The title compound is prepared by manganese dioxide oxidation of the 4-hydroxymethyl-group of (E)-1-[2-n-butyl-1-{(2-chlorophenyl)methyl}-4-hydroxymethyl-1H-imidazol-5-yl]-2-(1H-tetrazol-5-yl)-3-(2-thienyl)-1-propene, prepared in Example 18.

EXAMPLE 39

1-[1-(2-Adamantyl)ethyl-2-n-butyl-1H-imidazol-5-yl]-2-(1H-tetrazol-5-yl)-3-(2-thienyl)-1-propene A mixture of 2-(1-adamantyl)ethanol (10.7 g and diisopropylethylamine (11 ml) in dichloromethane (70 ml) was added to triflic anhydride (16.75 g) in dichloro methane (70 ml) at −78° C. under argon. After stirring the mixture at −78° C. for 45 minutes, 1-acetyl-2-n-butyl-5-(acetoxymethyl)imidazole in dichloromethane (50 ml) was added and the mixture was allowed to stand at room temperature for 4 days, then concentrated and heated on a steam bath with 10% sodium hydroxide (250 ml), diluted with 300 ml of water, extracted with dichloromethane, dried, filtered and concentrated to give an oil. Chromatography (silica gel) in methanol chloroform gives 5-acetoxymethyl-1-[2-(1-adamantyl)ethyl]-2-n-butylimidazole.

The above prepared compound (5.4 g) was stirred at room temperature with potassium hydroxide (5.2 g) in ethanol (200 ml) for one hour. The mixture was concentrated, poured into water, stirred and filtered to give 1-[2-(1-adamantyl)ethyl]-2-n-butyl-5-hydroxymethylimidazole. The hydroxymethyl-group was oxidized by refluxing the imidazole compound (51.1 g) with manganese dioxide (20.3 g) in toluene (200 ml) to give 1-[2-(1-adamantyl)ethyl]-2-n-butyl-imidazol-5-carboxaldehyde.

Diisopropylamine (0.563 g) was covered with 5 ml of tetrahydrofuran and 2 ml of 2.5M n-butyl lithium in hexane was added. The mixture was stirred for 15 minutes, then methyl 3-(2-thienyl)propenoate (0.89 g) in 3 ml of tetrahydrofuran was added. After 20 minutes, 1.04 g of 1-[2-(1-adamantyl)ethyl]-2-n-butyl-imidazol-5-carboxaldehyde in 3 ml of tetrahydrofuran was added and the mixture was stirred for 30 minutes at −78° C. The mixture was poured into 40 ml of saturated ammonium chloride in water, extracted with ether, dried over magnesium sulfate, filtered, concentrated and chromatographed on silica gel eluting with 70% ethyl acetate and 30% hexane to give methyl 3-[1-(2-(1-adamantyl)ethyl)2-n-butyl-1H-imidazol-5-yl]-3-hydroxy-2-(2-thienylmethyl)propanoate. To 1.27 g of this compound in dichloromethane (25 ml) was added 4-dimethylaminopyridine (1.25 g), then acetic anhydride (2.75 g) was added dropwise. The mixture was stirred for one hour, then poured into water and worked up to give 3-acetoxy-3-[1-(2-(1-adamantyl)ethyl)-2-n-butyl-1H-imidazol-5-yl]-2-(2-thienylmethyl)propanoate.

The above prepared compound (1.2 g) was heated with 1,8-diazabicyclo[5.4.0]undec-7-ene (1 ml) in toluene (20 ml) at 80° C. with stirring for one hour. The mixture was concentrated, then stirred with ether. The ether layer was decanted and dried, filtered, concentrated and chromatographed to give methyl 3-[1-(2-(1-adamantyl)ethyl)-2-n-butyl-1H-imidazol-5-yl]-2-(2-thienylmethyl)-2-propenoate.

This ester (0.63 g) was hydrolyzed in ethanol (10 ml) using potassium hydroxide (0.18 g) to give 3-[1-(2-adamantyl)ethyl)-2-n-butyl-1H-imidazol-5-yl]-2-(2-thienyl)methyl-2-propenoic acid.

The title tetrazole compound is prepared from the above acid by the procedure of Example 1.

EXAMPLE 40

(E)-1-[2-n-Butyl-1-{(2-chlorophenyl)methyl}-4-carboxy-1H-imidazol-5-yl]-2-(1H-tetrazol-5-yl)-3-(2-thienyl)-1-propene The title compound is prepard by oxidizing (E)-1-[2-n-butyl-1-{(2-chlorophenyl)methyl}-4-hydroxymethyl-1H-imidazol-5-yl]-2-(1H-tetrazol-5-yl}-3-(2-thienyl)-1-propene (prepared in Example 18) with an acidic aqueous solution containing chromic acid.

EXAMPLE 41

(E)-1-[2-n-Butyl-1-(2-chlorophenyl)methyl}-4-carbamoyl-1H-imidazol-5-yl]-2-(1H-tetrazol-5-yl)-3-(2-thienyl)-1-propene The title compound is prepared by treating (E)-1-[2-n-butyl-1-{(2-chlorophenyl)methyl}-4-carboxy-1H-imidazol-5-yl]-2-(1H-tetrazol-5-yl)-3-(2-thienyl)-1-propene with oxalyl chloride in methylene chloride at 0° C. to give the intermediate 4-chloroformyl imidazole which is then reacted with ammonium hydroxide.

EXAMPLE 42

(E)-1-[2-n-Butyl-1-{(2-chlorophenyl)methyl}-4-dimethylcarbamoyl-1H-imidazol-5-yl]-2-(1H-tetrazol-5-yl) 3-(2-thienyl)-1-propene Treating the 4-chloroformyl imidazole, prepared as in Example 38, with dimethylamine instead of ammonium hydroxide gives the title compound.

EXAMPLE 43

(E)-1-[2-n-Butyl-1-{(2-chlorophenyl)methyl}-1H-imidazol-5-yl]-2-(1H-tetrazol-5-yl)-3-(4-methoxyphenyl)-1-propene The title compound was prepared by the procedure of Example 1, using 4-methoxybenzyl chloride in place of 2-chloromethylthiophene; mp 168°–171° C.

EXAMPLE 44

(E)-1-[2-n-Butyl-1-{(2-chlorophenyl)methyl}-1H-imidazol-5-yl]-2-(1H-tetrazol-5-yl)-3-(4-hydroxyphenyl)-1-propene The title compound was prepared by reacting (E)-1-[2-n-butyl-1-{(2-chlorophenyl)methyl}-1H-imidazol-5-yl]-2-(1H-tetrazol-5-yl)-3-(4-methoxyphenyl)-1-propene with boron tribromide in methylene chloride at room temperature. The product was isolated as the hydrobromide salt; mp 218°–221° C.

EXAMPLE 45

(E)-1-[2-(1-Butenyl)-1-{(2-chlorophenyl)methyl}-1H-imidazol-5-yl]-2-(1H-tetrazol-5-yl)-3-(2-thienyl)-1-propene A mixture of 2-n-butyl-1-(2-chlorophenyl)methyl-1H-imidazol-5-carboxaldehyde and N-bromosuccinimide in carbon tetrachloride was irradiated to give the 2-(1-bromobutyl)imidazole which was dehydrobrominated by treating 1,8-diazabicyclo[4.5.0]undec-1-ene in tetrahydrofuran to give 2-(1-butenyl)-1-(2-chlorophenyl)-methyl-1H-imidazol-5-carboxyaldehyde. The above prepared imtermediate and the 3-(2-thienyl)propenoate of Example 1 in the procedure of Example 1 was used to give the title compound; mp 182°–184° C.

EXAMPLE 46

(E)-1-[2-n-Propyl-1-{(2-chlorophenyl)methyl}-1H-imidazol-5-yl]-2-(1H-tetrazol-5-yl)-3-(2-thienyl)-1-propene The title compound was prepared using the procedure of Example 1 replacing valeramidine methyl ether hydrochloride with butyramidine methyl-ether hydrochloride; mp 174°–175° C.

EXAMPLE 47

(E)-1-[2-n-Butyl-1-{(4-(1H-tetrazol-5-yl)phenyl)methyl}-1H-imidazol-5-yl]-2-(1H-tetrazol-5-yl)-3-(2-thienyl)-1-propene By the procedure of Example 1 [(ii) Method 2, (iii) and Method A (i–vi)] using 4-carbomethoxybenzyl alcohol in place of 2-chlorobenzyl-alcohol, the title compound was prepared; mp 227°–230° C.

EXAMPLE 48

(E)-1-[2-n-Butyl-1-{(4-carboxyphenyl))methyl}-1H-imidazol-5-yl]-2-(1H-tetrazol-5-yl)-3-(2-thienyl)-1-propene By the procedure of Example 1, Method B(i iii) using t-butyl 3-(2-thienyl)propanoate in place of methyl 3-(2-thienyl)propanoate and 2-n-butyl-1-(4-carbomethoxyphenyl)methyl-1H-imidazol-5-carboxaldehyde (prepared by the method of Example 1 [(ii) Method 2 and (iii)] using 4-carbomethoxybenzyl-alcohol in place of 2-chlorobenzyl alcohol) in place of 2-n-butyl-1-(2-chlorophenyl)methyl1H-imidazol-5-carboxaldehyde, t-butyl (E)-3-[2-n-butyl-1-[(4-carbomethoxy)phenyl)-methyl-1H-imidazol-5-yl]-2-[(2-thienyl)methyl]-propenoate was prepared. The t-butyl ester group was removed by acid hydrolysis with trifluoroacetic acid in methylene chloride. The tetrazole group was prepared following the procedure of Example 1, Method A (iv-)–(vi). Basic hydrolysis of the methyl-ester according to Example 1, Method A (iii), gave the title compound; mp 199°–200° C.

EXAMPLE 49

(E)-3-[1-{(2-Chlorophenyl)methyl}-2-propylthio-1H-imidazol-5-yl]-2-(1H-tetrazol-5-yl)-3-(2-thienyl)-1-propene (i)
5-carboxymethyl-1-(2-chlorophenyl)methyl-2-thio-1H-imidazole A solution of 2-chlorobenzylamine (14.2 g, 0.1 mol) and triethylamine 913.9 ml, 0.1 mol), in dimethylformamide (100 ml) was treated with methyl-chloroacetate (10.9 g, 0.1 mol), and the mixture was heated at 50° C. for 3.5 hours. The cooled reaction mixture was diluted with ether, the solids filtered and concentrated filtrate was flash chromatograhed over silica gel with 6:5 hexane in ethyl acetate to provide 15.3 g (71%) of homogeneous methyl 2-[N-(2-chlorophenyl)methyl]aminoacetate. This product (15.2 g, 0.071 mol) in mixed xylenes (100 ml) was treated with 98% formic acid (2.74 ml), 0.0711 mol) and the mixture was refluxed from 2.5 hours with a Dean-Stark water separator. Evaporation gave 17.1 g (99%) of methyl 2-[N (2-chlorophenyl)-methyl-N-formyl]aminoacetate. This formylated product (17.0 g, 0.071 mol) was dissolved in methyl formate (13.3 ml, 0.216 mol) and added dropwise to a sodium methoxide mixture prepared by adding sodium metal (1.79 g, 0.0778 g atom) to tetrahydrofuran (325 ml) followed by slow addition of methanol (3.15 ml, 0.0778 mol). The combined mixture was stirred at room temperature for 18 hours, then evaporated to dryness. This crude product was dissolved in 50% aqueous methanol (200 ml), treated with charcoal, filtered and the solution was cooled in ice. Concentrated hydrochloric acid followed by a solution of potassium thiocyanate (8.6 g, 0.0885 mol) in water (20 ml). The mixture was heated in an oil bath held at 90° C. for 2.5 hours, then cooled to 10° C. The precipitated solid was filtered, washed with cold ethanol water and dried at 60° C. to provide 14.7 g (74%) of 5-carboxymethyl-1-(2-chlorophenyl)methyl-2-thio-1H-imidazole; mp 72°–74° C.

(ii)
1-(2-chlorophenyl)methyl-5-carboxymethyl-2-propylthio-1H-imidazole

A mixture of 5-carboxymethyl-1-(2-chlorophenyl)-methyl-2-thio-1H-imidazole (2 g, 7.08 mol, ethyl acetate (20 ml), 5% sodium carbonate solution (40 ml) and propyl bromide (4 ml, 44 mmol) was heated at 60° C. for 18 hours. The organic layer was separated, dried over magnesium sulfate and concentrated to 2.23 g of crude product. Trituration with ether provided 1.63 g (71%) of 5-carboxymethyl-1-(2-chlorophenyl)methyl-2-propylthio-1H-imidazole; mp 68°–71° C. (from hexane).

(iii)
(E)-3-[1-(2-chlorophenyl)methyl-2-propylthio-1H-imidazol-5-yl]-2-(2-theinyl)methyl-2-propenoic acid A solution of 5-carboxymethyl-1-(2-chlorophenyl)-methyl-2-propylthio-1H-imidazole (3.74 g, 11.5 mmol) in dry tetrahydrofuran (50 ml) was cooled to 78° C. under argon, and a solution of diisobutyl-alumninum hydride in toluene (30 ml of 1M) was added dropwise. The mixture was stirred at −78° C. for 1.5 hours, then allowed to slowly warm to room temperature. The reation was quenched by pouring onto iced dilute acetic acid, the product was extracted into methylene chloride and the organic extracts were washed with water, 5% sodium carbonate solution and brine. The dried, concentrated product was a light tan solid (3.32 g). Crystallization from ethanol/water gave 1-(2-chlorophenyl)-methyl-5-hydroxymethyl-2-propylthio-1H-imidazole; mp 98°-101° C. The title compound is prepared by the procedure of Example 1 [(iii) Method A (i-vi)] using 1-(2-chlorophenyl)methyl-5-hydroxymethyl-2-propylthio-1H-imidazole in place of 2-n-butyl-1-(2-chlorophenyl)methyl-5-hydroxymethyl-1H-imidazole.

EXAMPLE 50

An oral dosage form for administering orally active Formula (I) compounds is produced by screening, mixing and filling into hard gelatin capsules the ingredients in proportions, for example, as shown below.

| Ingredients | Amounts |
| --- | --- |
| (E)-1-[2-n-butyl-1-{(2-chlorophenyl)-methyl}-1H-imidazol-5-yl]-2-(1H-tetrazol-5-yl)-3-(2-thienyl)-1-propene | 100 mg |
| magnesium stearate | 10 mg |
| lactose | 100 mg |

EXAMPLE 51

The sucrose, calcium sulfate dihydrate and orally active Formula (I) compounds are mixed and granulated with a 10% gelatin solution. The wet granules are screened, dried, mixed with the starch, talc and stearic acid, screened and compressed into a tablet.

| Ingredients | Amounts |
| --- | --- |
| (E)-1-[2-n-butyl-1-{(2-chlorophenyl)-methyl}-1H-imidazol-5-yl]-2-(1H-tetrazol-5-yl)-3-(3-thienyl)-1-propene | 75 mg |
| calcium sulfate dihydrate | 100 mg |
| sucrose | 15 mg |
| starch | 8 mg |
| talc | 4 mg |
| stearic acid | 2 mg |

EXAMPLE 52

(E)-1-[2-n-butyl-1-{(2-chlorophenyl)methyl}-1H-imidazol-5-yl]-2-(1H-tetrazol-5-yl)-3-(2-thienyl)-1-propene, is dispersed in 25 ml of normal saline to prepare an injectable preparation.

EXAMPLE 53

A topical opthamological solution for administering Formula (I) compounds is produced by mixing under sterile conditions the ingredients in proportions, for example, as shown below.

| Ingredients | Amounts (mg/mL) |
| --- | --- |
| (E)-1-[2-n-butyl-1-{2-chlorophenyl)methyl}-1H-imidazol-5-yl]-2-(1H-tetrazol-5-yl)-3-(3-thienyl)-1-propene | 1.0 |
| dibasic sodium phosphate | 10.4 |
| monobasic sodium phosphate | 2.4 |
| chlorobutanol | 5.0 |
| hydroxypropanol methylcellulose | 5.0 |
| sterile water | q.s. ad 1.0 mL |
| 1.0 N sodium hydroxide | q.s. ad pH 7.4 |

It is to be understood that the invention is not limited to the embodiments illustrated hereabove and the right to the illustrated embodiments and all modifications coming within the scope of the following claims is reserved.

What is claimed is:

1. A compound of the formula:

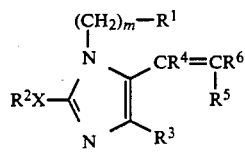

in which:

R[1] is adamantylmethyl, or phenyl, biphenyl, or naphthyl, with each aryl group being unsubstituted or substituted by one to three substituents selected from Cl, Br, F, I, $C_1$-$C_6$alkyl, nitro, $CO_2R^7$, $C_1$-$C_6$alkoxy, hydroxy, $SC_1$-$C_6$alkyl, $SO_2C_1$-$C_6$alkyl, tetrazol-5-yl, $SO_2NHR^7$, $NHSO_2R^7$, $SO_3H$, $PO(OR^7)_2$, $CONR^7R^7$, $CN$, $NR^7R^7$, $NR^7COH$, $NR^7COC_1$-$C_6$alkyl, $NR^7CON(R^7)_2$, $NR^7COW$, $SO_2W$, or W;

R[2] is $C_2$-$C_{10}$alkyl, $C_3$-$C_{10}$alkenyl, $(CH_2)_{0-8}$-$C_3$-$C_6$cycloalkyl, or $(CH_2)_{0-8}$phenyl unsubstituted or substituted by one to three substituents selected from $C_1$-$C_6$alkyl, nitro, Cl, Br, F, I, hydroxy, $C_1$-$C_6$alkoxy, $NR^7R^7$, $CO_2R^7$, $CN$, $CONR^7R^7$, W, $NR^7COH$, $NR^7COC_1$-$C_6$alkyl, $NR^7COW$, $SO_2W$, $SO_2C_1$-$C_6$alkyl, or $SC_1$-$C_6$alkyl;

X is a single bond, S, or O;

m is 0–4;

R[3] is hydrogen, Cl, Br, F, I, CHO, hydroxymethyl, $C_1$-$C_6$alkyl, $NR^7R^7$, $CO_2R^7$, $CONR^7R^7$, $NO_2$, $CN$, phenyl, or W;

R[4] and R[5] are each independently hydrogen, $C_1$-$C_8$alkyl, $C_3$-$C_6$cycloalkyl, thienyl-Y-, furyl-Y-, pyrazolyl-Y-, imidazolyl-Y-, thiazolyl-Y-, pyridyl-Y-, tetrazolyl-Y-, pyrrolyl-Y-, triazolyl-Y-, oxazolyl-Y-, isoxazolyl-Y-, or phenyl-Y-, with each aryl or heteroaryl group being unsubstituted or substituted by $C_1$-$C_6$alkyl, $C_1$-$C_6$alkoxy, Cl, Br, F, I, $NR^7R^7$, $CO_2R^7$, $SO_2NHR^7$, $SO_3H$, OH, $NO_2$, $CONR^7R^7$, W, $SO_2C_1$-$C_6$alkyl, $SO_2W$, $SC_1$-$C_6$alkyl, $NR^7COH$, $NR^7COW$, or $NR^7COC_1$-$C_6$alkyl;

Y is $C_1$-$C_6$alkyl which is straight or branched or a single bond;

R[6] is Z-tetrazol-5-yl;

Z is a single bond, vinyl, or methylene unsubstituted or substituted by $C_1$-$C_4$alkyl, one or two benzyl groups, thienylmethyl, or furylmethyl;

W is $C_nF_{2n+1}$, wherein n is 1–4; and
each $R^7$ independently is hydrogen or $C_1$–$C_6$alkyl;
or a pharmaceutically acceptable salt thereof.

2. A compound of claim 1 in which one of $R^4$ and $R^5$ is hydrogen or $Cl_1$–$C_6$alkyl.

3. A compound of claim 2 in which:
$R^1$ is phenyl unsubstituted or substituted by one to three substituents selected from chloro, fluoro, nitro, methyl, trifluoromethyl, methoxy; hydroxy, sulfonamido, sulfamyl, cyano, carboxy, carboC$_{1-6}$alkoxy, carbamoyl, or tetrazol-5-yl;
$R^2$ is $C_2$–$C_8$alkyl;
X is a single bond or S;
m is one or two;
$R^3$ is hydrogen, chloro, fluoro, or trifluoromethyl;
$R^4$ is hydrogen or $C_1$–$C_4$alkyl;
$R^5$ is thienylmethyl unsubstituted or substituted by methyl, or benzyl unsubstituted or substituted by methoxy or hydroxy; and
$R^6$ is tetrazol-5-yl;
or a pharmaceutically acceptable salt thereof.

4. A compound of claim 3 which is the E isomer, wherein the tetrazole and imidazole groups are trans to each other.

5. The compound of claim 4 which is (E)-1-[2-n-butyl-1-{(2-chlorophenyl)methyl}-1H-imidazol-5-yl]-2-(1H-tetrazol-5-yl)-3-(2-thienyl)-1-propene or a pharmaceutically acceptable salt thereof.

6. The compound of claim 4 which is (E)-1-[2-n-butyl-1-{(4-carboxyphenyl)methyl}-1H-imidazol-5-yl]-2-(1H-tetrazol-5-yl)-3-(2-thienyl)-1-propene or a pharmaceutically acceptable salt thereof.

7. The compound of claim 4 which is:
(E)-1-[2-n-butyl-1-{(2-chlorophenyl)methyl}-1H-imidazol-5-yl]-2-(1H-tetrazol-5-yl)-3-(5-methyl-2-thienyl)-1-propene;
(E)-1-[2-n-butyl-1-{(2-nitrophenyl)methyl}-1H-imidazol-5-yl]-2-(1H-tetrazol-5-yl)-3-(2-thienyl)-1-propene;
(E)-1-[2-n-butyl-1-[(2-trifluoromethylphenyl)methyl)-1H-imidazol-5-yl]-2-(1H-tetrazol-5-yl)-3-(2-thienyl)-1-propene;
(E)-1-[2-n-butyl-1-{(2,3-dichlorophenyl)methyl}-1H-imidazol-5-yl]-2-(1H-tetrazol-5-yl)-3-(2-thienyl)-1-propene;
(E)-1-[2-n-butyl-1-{(2-chlorophenyl)methyl}-4-fluoro-1H-imidazol-5-yl]-2-(1H-tetrazol-5-yl)-3-(2-thienyl)-1-propene;
(E)-1-[2-n-butyl-1-{(2-chlorophenyl)methyl}-1H-imidazol-5-yl]-2-(1H-tetrazol-5-yl)-3-(3-thienyl)-1-propene;
(E)-1-[2-n-butyl-1-{(2-chlorophenyl)methyl}-1H-imidazol-5-yl]-2-(1H-tetrazol-5-yl)-3-(4-methoxyphenyl)-1-propene;
(E)-1-[2-n-butyl-1-{(2-chlorophenyl)methyl}-1H-imidazol-5-yl]-2-(1H-tetrazol-5-yl)-3-(4-hydroxyphenyl)-1-propene;
(E)-1-[2-(1-butenyl)-1-{(2-chlorophenyl)methyl}-1H-imidazol-5-yl]-3-(2-thienyl)-1-propene;
(E)-1-[2-n-propyl-1-{(2-chlorophenyl)methyl}-1H-imidazol-5-yl]-2-(1H-tetrazol-5-yl)-3-(2-thienyl)-1-propene; or
(E)-1-[2-n-butyl-1-{(4-(1H-tetrazol-5-yl)phenyl)methyl}-1H-imidazol-5-yl]-2-(1H-tetrazol-5-yl)-3-(2-thienyl)-1-propene; or a pharmaceutically acceptable salt thereof.

8. A pharmaceutical composition comprising a pharmaceutical carrier and a compound of claim 1.

9. A pharmaceutical composition of claim 8 in which the compound is (E)-1-[2-n-butyl-1-{(2-chlorophenyl)methyl}-1H-imidazol-5-yl]-2-(1H-tetrazol-5-yl)-3-(2-thienyl)-1-propene.

10. A pharmaceutical composition of claim 8 in which the compound is (E)-1-[2-n-butyl-1-{(4-carboxyphenyl)methyl}-1H-imidazol-5-yl]-2-(1H-tetrazol-5-yl) 1-propene.

11. A pharmaceutical composition of claim 8 in which the compound is:
(E)-1-[2-n-butyl-1-{(2-chlorophenyl)methyl}-1H-imidazol-5-yl]-2-(1H-tetrazol-5-yl)-3-(5-methyl-2-thienyl)-1-propene;
(E)-1-[2-n-butyl-1-{(2-nitrophenyl)methyl}-1H-imidazol-5-yl]-2-(1H-tetrazol-5-yl)-3-(2-thienyl)-1-propene;
(E)-1-[2-n-butyl-1-{(2-trifluoromethylphenyl)methyl}-1H-imidazol-5-yl]-2-(1H-tetrazol-5-yl)-3-(2-thienyl)-1-propene;
(E)-1-[2-n-butyl-1-[(2,3-dichlorophenyl)methyl}-1H-imidazol-5-yl]-2-(1H-tetrazol-5-yl)-3-(2-thienyl)-1-propene;
(E)-1-[2-n-butyl-1-(2-chlorophenyl)methyl}-4-fluoro-1H-imidazol-5-yl]-2-(1H-tetrazol-5-yl)-3-(2-thienyl)-1-propene;
(E)-1-[2-n-butyl-1-{(2-chlorophenyl)methyl}-1H-imidazol-5-yl]-2-(1H-tetrazol-5-yl)-3-(3-thienyl)-1-propene;
(E)-1-[2-n-butyl-1-{(2-chlorophenyl)methyl}-1H-imidazol-5-yl]-2-(1H-tetrazol-5-yl)-3-(4-methoxyphenyl)-1-propene;
(E)-1-[2-n-butyl-1-{(2-chlorophenyl)methyl}-1H-imidazol-5-yl]-2-(1H-tetrazol-5-yl)-3-(4-hydroxyphenyl)-1-propene;
(E)-2-[2-(1-butenyl)-1-{(2-chlorophenyl)methyl}-1H-imidazol-5-yl]-2-(1H-tetrazol-5-yl)-3-(2-thienyl)-1-propene;
(E)-1-[2-n-propyl-1-{(2-chlorophenyl)methyl}-1H-imidazol-5-yl]-2-(1H-tetrazol-5-yl)-3-(2-thienyl)-1-propene; or
(E)-1-[2-n-butyl-1-{(4-(1H-tetrazol-5-yl)phenyl)methyl}-1H-imidazol-5-yl]-2-(1H-tetrazol-5-yl)-3-(2-thienyl)-1-propene.

12. A method of antagonizing angiotensin II which comprises administering to a subject in need thereof an effective amount of a compound of claim 1.

13. A method of producing antihypertensive activity which comprises administering to a subject in need thereof an effective amount of a compound of claim 1.

14. A method of treating congestive heart failure by administering to a subject in need thereof an effective amount of a compound of claim 1.

15. A method of treating renal failure by administering to a subject in need thereof an effective amount of a compound of claim 1.

16. A method of treating glaucoma by administering to a subject in need thereof an effective amount of a compound of claim 1.

* * * * *

UNITED STATES PATENT AND TRADEMARK OFFICE
CERTIFICATE OF CORRECTION

PATENT NO. : 5,177,096
DATED : January 5, 1993
INVENTOR(S) : Keenan, Weinstock

It is certified that error appears in the above-identified patent and that said Letters Patent is hereby corrected as shown below:

In claim 1, column 41, line 5; replace "$Cl_1-C_6 alkyl$" with --- $C_1-C_6 alkyl$ ---.

In claim 7, column 41, line 58; replace "(E)-1-[2-(1-butenyl)-1-{(2-chlorophenyl)methyl}-1H-imidazol-5-yl)-3-(2-thienyl)-1-propene" with ---
(E)-1-[2-(1-butenyl)-1-{(2-chlorophenyl)methyl}-1H-imidazol-5-yl]-2-(1H-tetrazol-5-yl)-3-(2-thienyl)-1-propene; ---.

Column 42, line 10, should read as follows:

(E)-1-[2-n-butyl-1-{(4-carboxyphenyl)-methyl}-1H-imidazol-5-yl]-2-(1H-tetrazol-5-yl)-3-(2-thienyl)-1-propene.

Signed and Sealed this

Fifth Day of April, 1994

Attest:

BRUCE LEHMAN

Attesting Officer

Commissioner of Patents and Trademarks